(12) United States Patent
Schroeder et al.

(10) Patent No.: US 11,279,955 B2
(45) Date of Patent: Mar. 22, 2022

(54) PROCESS FOR PRODUCING AN ORGANIC COMPOUND

(71) Applicant: BASF SE, Ludwigshafen am Rhein (DE)

(72) Inventors: Hartwig Schroeder, Ludwigshafen (DE); Stefan Haefner, Ludwigshafen (DE); Oskar Zelder, Ludwigshafen (DE); Christoph Wittmann, Saarbrücken (DE); Anna Christine Schroer, Ludwigshafen (DE); Birgit Hoff, Ludwigshafen (DE); Nico Boehmer, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 65 days.

(21) Appl. No.: 16/614,772

(22) PCT Filed: May 18, 2018

(86) PCT No.: PCT/EP2018/063159
§ 371 (c)(1),
(2) Date: Nov. 18, 2019

(87) PCT Pub. No.: WO2018/211093
PCT Pub. Date: Nov. 22, 2018

(65) Prior Publication Data
US 2020/0181653 A1    Jun. 11, 2020

(30) Foreign Application Priority Data

May 19, 2017  (EP) .................................... 17171894

(51) Int. Cl.
| | | |
|---|---|---|
| *C12N 1/20* | (2006.01) | |
| *C12P 7/18* | (2006.01) | |
| *C12P 7/46* | (2006.01) | |

(52) U.S. Cl.
CPC . *C12P 7/18* (2013.01); *C12N 1/20* (2013.01)

(58) Field of Classification Search
None
See application file for complete search history.

(56) References Cited

U.S. PATENT DOCUMENTS

| | | | |
|---|---|---|---|
| 2006/0276674 A1 | 12/2006 | Kushiku et al. | |
| 2010/0159543 A1 | 6/2010 | Scholten et al. | |
| 2011/0269183 A1* | 11/2011 | Lee ........................... | C12P 7/56 435/69.1 |
| 2013/0337519 A1* | 12/2013 | Dole ......................... | C12R 1/01 435/145 |
| 2020/0181653 A1* | 6/2020 | Schroeder ................. | C12R 1/01 |

FOREIGN PATENT DOCUMENTS

| | | |
|---|---|---|
| EP | 1005562 A1 | 6/2000 |
| EP | 2360137 A1 | 8/2011 |
| WO | 2005030973 A1 | 4/2005 |
| WO | 2005052135 A1 | 6/2005 |
| WO | 2007019301 A2 | 2/2007 |
| WO | 2008010373 A1 | 1/2008 |
| WO | 2009024294 A1 | 2/2009 |
| WO | 2009078687 A2 | 6/2009 |
| WO | 2010092155 A1 | 8/2010 |
| WO | 2011043443 A1 | 4/2011 |
| WO | 2011064151 A1 | 6/2011 |
| WO | 2011082378 A2 | 7/2011 |
| WO | 2011123268 A1 | 10/2011 |
| WO | 2015118051 A1 | 8/2015 |

OTHER PUBLICATIONS

Kuhnert et al. "*Basfia succiniciproducens* gen. nov., sp. nov., a new member of the family Pasteurellaceae isolated from bovine rumen" International Journal of Systematic and Evolutionary Microbiology (2010), 60, 44-50.

Kilimann et al. "Protection by sucrose against heat-induced lethal and sublethal injury of *Lactococcus lactis*: An FT-IR study" Biochimica et Biophysica Acta 1764 (2006) 1188-1197.

Helanto et al.: "Characterization of genes involved in fructose utilization by Lactobacillus fermentum"; Arch. Microbiol. (2006), vol. 186, p. 51-59.

Wong et al. "Real-time PCR for mRNA quantitation", BioTechniques, vol. 39, No. 1, Jul. 2005, pp. 75-85.

Leenhouts et al., "Campbell-Like Integration of Heterologous Plasmid DNA into the Chromosome of *Lactococcus lactis* subsp. *lactis*" Appl Env Microbiol. (1989), vol. 55, pp. 394-400.

Asanuma et al. "Effects of pH and Energy Supply on Activity and Amount of Pyruvate-Formate-Lyase in *Streptococcus bovis*", Appl. Environ. Microbiol. (2000), vol. 66, pp. 3773-3777.

Bergmeyer et al. "Methods of Enzymatic Analysis", 1983, 3rd Edition, vol. III, pp. 126-133, Verlag Chemie, Weinheim.

Song et al. "Production of succinic acid by bacterial fermentation" Enzyme and Microbial Technology 39 (2006) 352-361.

(Continued)

*Primary Examiner* — Richard C Ekstrom
(74) *Attorney, Agent, or Firm* — Armstrong Teasdale LLP

(57) ABSTRACT

Described herein is a process of producing an organic compound, the process including: I) cultivating a genetically modified microorganism in a culture medium including sucrose as an assimilable carbon source to allow the genetically modified microorganism to produce the organic compound, and II) recovering the organic compound from the fermentation broth obtained in process step I) The genetically modified microorganism includes A) at least one genetic modification that leads to an increased activity of the enzyme encoded by the rbsK-gene, compared to the original microorganism that has not been genetically modified, and the original microorganism belongs to the family Pasteurellaceae. Also described herein are a genetically modified microorganism and the use thereof for the fermentative production of an organic compound from sucrose as an assimilable carbon source.

19 Claims, No Drawings

Specification includes a Sequence Listing.

(56) References Cited

OTHER PUBLICATIONS

Becker et al., "Systems-Wide Analysis and Engineering of Metabolic Pathway Fluxes in Bio-Succinate Producing Basfia Succiniciproducens" Biotechnology and Bioengineering, vol. 110 (2013), pp. 3013-3023.
Becker et al., "From zero to hero—Design-based systems metabolic engineering of Corynebacterium glutamicum for L-lysine production" Metabolic Engineering, vol. 13 (2011), pp. 159-168.
Kind et al., "Systems-wide metabolic pathway engineering in Corynebacterium glutamicum for bio-based production ol diaminopentane" Metabolic Engineering, vol. 12 (2010), pp. 341-351.
Frey, "Construction of a broad host range shuttle vector for gene cloning and expression in Actinobacillus oleuropneumoniae and other Pasteurellaceae" Res Microbiol. vol. 143 (3) (1992), pp. 263-269.
Wook et al. "Homo-succinic acid production by metabolically engineered Mannheimia succiniciproducens", Metabolic Engineering, vol. 38, Oct. 13, 2016, pp. 409-417.

* cited by examiner

PROCESS FOR PRODUCING AN ORGANIC COMPOUND

CROSS-REFERENCE TO RELATED APPLICATIONS

This application is a U.S. National Phase Application of International Patent Application No. PCT/EP2018/063159, filed May 18, 2018, which claims the benefit of priority to European Patent Application No. 17171894.3, filed May 19, 2017, the entire contents of which are hereby incorporated by reference herein.

FIELD OF THE INVENTION

The present invention relates to a process for producing an organic compound, preferably succinic acid, to a genetically modified microorganism and to the use of the genetically modified microorganism for the fermentative production of an organic compound, preferably succinic acid.

BACKGROUND

Organic compounds such as small dicarboxylic acids having 6 or fewer carbons are commercially significant chemicals with many uses. For example, the small diacids include 1,4-diacids, such as succinic acid, malic acid and tartaric acid, and the 5-carbon molecule itaconic acid. Other diacids include the two carbon oxalic acid, three carbon malonic acid, five carbon glutaric acid and the 6 carbon adipic acid and there are many derivatives of such diacids as well.

As a group the small diacids have some chemical similarity and their uses in polymer production can provide specialized properties to the resin. Such versatility enables them to fit into the downstream chemical infrastructure markets easily. For example, the 1,4-diacid molecules fulfill many of the uses of the large scale chemical maleic anhydride in that they are converted to a variety of industrial chemicals (tetrahydrofuran, butyrolactone, 1,4-butanediol, 2-pyrrolidone) and the succinate derivatives succindiamide, succinonitrile, diaminobutane and esters of succinate. Tartaric acid has a number of uses in the food, leather, metal and printing industries. Itaconic acid forms the starting material for production of 3-methylpyrrolidone, methyl-BDO, methyl-THF and others.

In particular, succinic acid or succinate—these terms are used interchangeably herein—has drawn considerable interest because it has been used as a precursor of many industrially important chemicals in the food, chemical and pharmaceutical industries. In fact, a report from the U.S. Department of Energy reports that succinic acid is one of 12 top chemical building blocks manufactured from biomass. Thus, the ability to make diacids in bacteria would be of significant commercial importance.

WO-A-2009/024294 discloses a succinic acid producing bacterial strain, being a member of the family of Pasteurellaceae, originally isolated from rumen, and capable of utilizing glycerol as a carbon source and variant and mutant strains derived there from retaining said capability, in particular, a bacterial strain designated DD1 as deposited with DSMZ (Deutsche Sammlung von Mikroorganismen and Zellkulturen GmbH, Inhoffenstr. 7B, D-38124 Braunschweig, Germany) having the deposit number DSM 18541 (ID 06-614) and having the ability to produce succinic acid. The DD1-strain belongs to the species *Basfia succiniciproducens* and the family of Pasteurellaceae as classified by Kuhnert et al., 2010. Mutations of these strains, in which the ldhA-gene and/or the pflD- or the pflA-gene have been disrupted, are disclosed in WO-A-2010/092155, these mutant strains being characterized by a significantly increased production of succinic acid from carbon sources such as glycerol or mixtures of glycerol and carbohydrates such as maltose, under anaerobic conditions compared to the DD1-wildtype disclosed in WO-A-2009/024294.

However, bio-based succinate still faces the challenge of becoming cost competitive against petrochemical-based alternatives. In order to develop the bio-based industrial production of succinic acid, it will be important to grow the cells in a low cost medium, and the working strain optimally should be able to metabolize a wide range of low-cost sugar feedstock to produce succinic acid in good yields so that the cheapest available raw materials can be used.

Sucrose (commonly known as sugar) is a disaccharide consisting of glucose and fructose, and it is a carbon source that is very abundant in nature and is produced from all plants having photosynthesis ability. Particularly, sugarcane and sugar beet contain large amounts of sucrose, and more than 60% of the world's sucrose is currently being produced from sugarcane. Particularly, sucrose is produced at a very low cost, because it can be industrially produced through a simple process of evaporating/concentrating extracts obtained by mechanical pressing of sugarcanes. Sucrose as a raw material for producing chemical compounds through microbial fermentation is thus inexpensive and it also functions to protect the cell membrane from an external environment containing large amounts of desired metabolites, thus producing high-concentrations of desired metabolites as shown by Kilimann et al. (*Biochimica et Biophysica Acta*, 1764, 2006).

WO 2015/118051 A1 discloses a modified microorganism having, compared to its wildtype, a reduced activity of the enzyme that is encoded by the fruA-gene, wherein the wildtype from which the modified microorganism has been derived belongs to the family of Pasteurellaceae, The fruA-gene encodes for a fructose-specific phosphotransferase (fructose PTS). Compared to the wildtype cell (i. e. the above described DD1-strain) the recombinant cell in which the fruA-gene has been deleted is characterized by an increased yield of succinic acid when being cultured in the presence of sucrose as the sole or predominant carbon source. However, in view of the economic efficiency of the fermentative production of succinic acid from sucrose as the carbon source it is still desirable to provide further modified microorganisms with are able to produce large amount of succinic acid from sucrose and which—compared to the modified strains known from the prior art—preferably produce even more succinic acid from sucrose.

BRIEF DESCRIPTION

It was therefore an object of the present invention to overcome the disadvantages of the prior art.

In particular, it was an object of the present invention to provide a process for producing an organic compound such as succinic acid by means of which high carbon yields can be achieved when using sucrose as the carbon source.

It was also an object of the present invention to provide a genetically modified microorganism that, compared to the original cell from which it has been derived by genetic modification, allows the production of an organic compound such as succinic acid from sucrose as the carbon source with higher carbon yields.

DETAILED DESCRIPTION

A contribution to achieving the abovementioned aims is provided by a process of producing an organic compound, preferably succinic acid, the process comprising
I) cultivating a genetically modified microorganism in a culture medium comprising sucrose as an assimilable carbon source to allow the genetically modified microorganism to produce the organic compound,
II) recovering the organic compound from the fermentation broth obtained in process step I),
wherein the genetically modified microorganism comprises
A) at least one genetic modification that leads to an increased activity of the enzyme encoded by the rbsK-gene, compared to the original microorganism that has not been genetically modified,
and wherein the original microorganism belongs to the family Pasteurellaceae.

Surprisingly, it has been discovered that microorganisms of the family Pasteurellaceae comprising at least one genetic modification that leads to an increased activity of the enzyme encoded by the rbsK-gene (encoding for an ATP-dependent fructokinase; EC 2.7.1.4) are characterized by an increased production of organic compounds such as succinic acid from sucrose as the sole or predominant carbon source, compared to the original microorganisms that have not been genetically modified. If, in addition to this genetic modification, the modified microorganisms further comprise at least one genetic modification that leads to a reduced activity of the enzyme encoded by the fruA-gene (encoding for a fructose-specific phosphotransferase system; EC 2.7.1.202), the production of organic compounds such as succinic acid from sucrose can even be further increased.

In the process according to the present invention a genetically modified microorganism is used that comprises
A) at least one genetic modification that leads to an increased activity of the enzyme encoded by the rbsK-gene, compared to the original microorganism that has not been genetically modified, wherein the original microorganism belongs to the family Pasteurellaceae.

Such a genetically modified microorganism is obtainable by a process at least comprising the process steps:
i) providing an original microorganism of the family Pasteurellaceae;
ii) genetically modifying the microorganism in such a way that the activity of the enzyme encoded by the rbsK-gene is increased;
iii) optionally performing further genetic modifications of the microorganism that lead to an increased or reduced activity of one or more further enzymes being different from the enzyme encoded by the rbsK-gene, wherein process step iii) can be performed at any time after process step i) (particularly before process step ii), after process step ii) or before and after process step ii)).

The term "original microorganism" as used herein preferably refers to the so called "wildtype"-strain. The term "wildtype" refers to a microorganism whose genome, in particular whose rbsK-gene and whose regulatory elements of the rbsK-gene, is/are present in a state as generated naturally as the result of evolution. As a consequence, the term "wildtype" preferably does not cover those microorganisms whose gene sequences have at least in part been modified by man by means of recombinant methods. The term "genetically modified microorganism" thus includes a microorganism which has been genetically altered, modified or engineered (e.g., genetically engineered) such that it exhibits an altered, modified or different genotype and/or phenotype (e. g., when the genetic modification affects coding nucleic acid sequences of the microorganism) as compared to the naturally-occurring wildtype microorganism from which it was derived. According to a particular preferred embodiment of the genetically modified microorganism used in the process of the present invention the genetically modified microorganism is a recombinant microorganism, which means that the microorganism has been obtained using recombinant DNA. The expression "recombinant DNA" as used herein refers to DNA sequences that result from the use of laboratory methods (molecular cloning) to bring together genetic material from multiple sources, creating sequences that would not otherwise be found in biological organisms. An example of such a recombinant DNA is a plasmid into which a heterologous DNA-sequence has been inserted.

The original microorganism from which the genetically modified microorganism has been derived by the above described genetic modification belongs to the family Pasteurellaceae. Pasteurellaceae comprise a large family of Gram-negative Proteobacteria with members ranging from bacteria such as *Haemophilus influenzae* to commensals of the animal and human mucosa. Most members live as commensals on mucosal surfaces of birds and mammals, especially in the upper respiratory tract. Pasteurellaceae are typically rod-shaped, and are a notable group of facultative anaerobes. They can be distinguished from the related Enterobacteriaceae by the presence of oxidase, and from most other similar bacteria by the absence of flagella. Bacteria in the family Pasteurellaceae have been classified into a number of genera based on metabolic properties and there sequences of the 16S RNA and 23S RNA. Many of the Pasteurellaceae contain pyruvate-formate-lyase genes and are capable of anaerobically fermenting carbon sources to organic acids.

In this context it is particularly preferred that the original microorganism belongs to the genus *Basfia* and it is particularly preferred that it belongs to the species *Basfia succiniciproducens*.

Most preferably, the original microorganism is *Basfia succiniciproducens*-strain DD1 deposited under the Budapest Treaty with DSMZ (Deutsche Sammlung von Mikroorganismen and Zellkulturen, GmbH), Germany, having the deposit number DSM 18541. This strain has been originally isolated from the rumen of a cow of German origin. *Pasteurella* bacteria can be isolated from the gastro-intestinal tract of animals and, preferably, mammals. The bacterial strain DD1, in particular, can be isolated from bovine rumen and is capable of utilizing glycerol (including crude glycerol) as a carbon source. Further strains of the genus *Basfia* that can be used for preparing the modified microorganism according to the present invention are the *Basfia*-strain that has been deposited under the deposit number DSM 22022 or the *Basfia*-strains that have been deposited with the Culture Collection of the University of Goteborg (CCUG), Sweden, having the deposit numbers CCUG 57335, CCUG 57762, CCUG 57763, CCUG 57764, CCUG 57765 or CCUG 57766. Said strains have been originally isolated from the rumen of cows of German or Swiss origin.

In this context it is particularly preferred that the original microorganism has a 16S rDNA of SEQ ID NO: 1 or a sequence, which shows a sequence homology of at least 96%, at least 97%, at least 98%, at least 99% or at least 99.9% with SEQ ID NO: 1. It is also preferred that the original microorganism has a 23S rDNA of SEQ ID NO: 2 or a sequence, which shows a sequence homology of at least 96%, at least 97%, at least 98%, at least 99% or at least 99.9% with SEQ ID NO: 2.

The identity in percentage values referred to in connection with the various polypeptides or polynucleotides to be used for the modified microorganism according to the present invention is, preferably, calculated as identity of the residues over the complete length of the aligned sequences, such as, for example, the identity calculated (for rather similar sequences) with the aid of the program needle from the bioinformatics software package EMBOSS (Version 5.0.0, http://emboss.source-forge.net/what/) with the default parameters which are, i.e. gap open (penalty to open a gap): 10.0, gap extend (penalty to extend a gap): 0.5, and data file (scoring matrix file included in package): EDNAFUL.

It should be noted that the original microorganism from which the genetically modified microorganism has been derived is not limited to one of the above mentioned strains, especially not to *Basfia succiniciproducens*-strain DD1, but may also comprise variants of these strains. In this context the expression "a variant of a strain" comprises every strain having the same or essentially the same characteristics as the wildtype-strain. In this context it is particularly preferred that the 16 S rDNA of the variant has an identity of at least 90%, preferably at least 95%, more preferably at least 99%, more preferably at least 99.5%, more preferably at least 99.6%, more preferably at least 99.7%, more preferably at least 99.8% and most preferably at least 99.9% with the wildtype from which the variant has been derived. It is also particularly preferred that the 23 S rDNA of the variant has an identity of at least 90%, preferably at least 95%, more preferably at least 99%, more preferably at least 99.5%, more preferably at least 99.6%, more preferably at least 99.7%, more preferably at least 99.8% and most preferably at least 99.9% with the wildtype from which the variant has been derived. A variant of a strain in the sense of this definition can, for example, be obtained by treating the wildtype-strain with a mutagenizing chemical agent, X-rays, or UV light.

According to a preferred embodiment of the genetically modified microorganism the rbsK-gene comprises a nucleic acid selected from the group consisting of:

a1) nucleic acids having the nucleotide sequence of SEQ ID NO: 3;
b1) nucleic acids encoding the amino acid sequence of SEQ ID NO: 4;
c1) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of a1) or b1), the identity being the identity over the total length of the nucleic acids of a1) or b1);
d1) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of a1) or b1), the identity being the identity over the total length of amino acid sequence encoded by the nucleic acids of a1) or b1);
e1) nucleic acids capable of hybridizing under stringent conditions with a complementary sequence of any of the nucleic acids according to a1) or b1); and
f1) nucleic acids encoding the same protein as any of the nucleic acids of a1) or b1), but differing from the nucleic acids of a1) or b1) above due to the degeneracy of the genetic code.

The term "hybridization" as used herein includes "any process by which a strand of nucleic acid molecule joins with a complementary strand through base pairing" (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules.

As used herein, the term "Tm" is used in reference to the "melting temperature". The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41(% G+C), when a nucleic acid molecule is in aqueous solution at 1 M NaCl (see e.g., Anderson and Young, Quantitative Filter Hybridization, in Nucleic Acid Hybridization (1985)). Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term "stringency conditions" refers to conditions, wherein 100 contiguous nucleotides or more, 150 contiguous nucleotides or more, 200 contiguous nucleotides or more or 250 contiguous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably at 65° C., with a specific nucleic acid molecule (DNA; RNA, ssDNA or ssRNA). Preferably, the hybridizing conditions are equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. Preferably, the complementary nucleotides hybridize with a fragment or the whole fruA nucleic acids. Alternatively, preferred hybridization conditions encompass hybridization at 65° C. in 1×SSC or at 42° C. in 1×SSC and 50% formamide, followed by washing at 65° C. in 0.3×SSC or by hybridization at 50° C. in 4×SSC or at 40° C. in 6×SSC and 50% formamide, followed by washing at 50° C. in 2×SSC. Further preferred hybridization conditions are 0.1% SDS, 0.1 SSD and 65° C.

Nucleic acid having the nucleotide sequence of SEQ ID NO: 3 corresponds to the rbsK-gene of *Basfia succiniciproducens*-strain DD1.

According to a particularly preferred embodiment of the genetically modified microorganism that is used in the process according to the present invention the genetically modified microorganism additionally comprises B) at least one genetic modification that leads to a reduced activity of the enzyme encoded by the fruA-gene, compared to the original microorganism that has not been genetically modified.

In the original microorganism from which the modified microorganism has been derived the fruA-gene preferably comprises a nucleic acid selected from the group consisting of:
a2) nucleic acids having the nucleotide sequence of SEQ ID NO: 5;
b2) nucleic acids encoding the amino acid sequence of SEQ ID NO: 6;
c2) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of a2) or b2), the identity being the identity over the total length of the nucleic acids of a2) or b2);
d2) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of a2) or b2), the identity being the identity over the total length of amino acid sequence encoded by the nucleic acids of a2) or b2);
e2) nucleic acids capable of hybridizing under stringent conditions with a complementary sequence of any of the nucleic acids according to a2) or b2); and
f2) nucleic acids encoding the same protein as any of the nucleic acids of a2) or b2), but differing from the nucleic acids of a2) or b2) above due to the degeneracy of the genetic code.

Nucleic acid having the nucleotide sequence of SEQ ID NO: 5 corresponds to the fruA-gene of *Basfia succiniciproducens*-strain DD1.

Increased Fructokinase-Activity

The genetically modified microorganisms that is used in the process according to the present invention comprises A) at least one genetic modification that leads to an increased activity of the enzyme encoded by the rbsK-gene, compared to the original microorganism that has not been genetically modified. Such a genetic modification can, for example, be a modification of the rbsK-gene itself and/or a modification of a regulatory element of the rbsK-gene, wherein the modification of the rbsK-gene and/or the modification of a regulatory element of the rbsK-gene lead/leads to an increased activity of the enzyme encoded by the rbsK-gene, compared to the original microorganism in which the rbsK-gene and/or the regulatory element of the rbsK-gene have/has not been modified.

The increase of the enzyme activity ($\Delta_{activity}$) is—in case of an original microorganism which already has a certain activity of fructokinase—preferably defined as follows:

$$\Delta_{activity} = \left( \frac{\text{activity of the genetically modified microorganism}}{\text{activity of the orginal microorganism}} \times 100\% \right) - 100\%$$

wherein, when determining $\Delta_{activity}$, the activity in the original microorganism and the activity in the modified microorganism are determined under exactly the same conditions. The activity of fructokinase that is encoded by the rbsK-gene can be determined as disclosed by Helanto et al.: "*Characterization of genes involved in fructose utilization by Lactobacillus fermentum*"; Arch. Microbiol. (2006), Vol. 186, p. 51-59.

The increased activity of fructokinase can be an increase of the enzymatic activity by 1 to 10000%, compared to the activity of said enzyme in the wildtype of the microorganism, or an increase of the enzymatic activity by at least 50%, or at least 100%, or at least 200%, or at least 300%, or at least 400%, or at least 500%, or at least 600% or at least 700%, or at least 800%, or at least 900%, or at least 1000%, or at least 5000%. Preferably, the increase of the activity of an enzyme is in the range of 10 to 1000%, more preferably in the range of 100 to 500%.

An increased fructokinase-activity can be accomplished by a genetic modification of the rbsK-gene itself, for example by increasing the copy number of the rbsK-gene, by using a gene or allele which codes for a corresponding enzyme having an increased activity or by introducing one or more gene mutations which lead to an increased activity of fructokinase. Such mutations can again be generated undirected either by classical methods, such as evolutionary adoption, UV irradiation or mutagenic chemicals, or targeted by genetic engineering methods such as deletion (s), insertion (s) and/or nucleotide exchange(s) by side directed mutagenesis. Also, an increased fructokinase-activity can be accomplished by a modification of regulatory elements of the rbsK-gene, such as a genetic modification of the rbsK-promoter sequence or a modification of regulatory proteins, suppressors, enhancers, transcriptional activators and the like involved in transcription of the rbsK-gene and/or the translation of the gene product. In this context it is, for example, possible to use a promoter sequence that, compared to the promoter sequence in the original microorganism, is stronger. It is, of course, also possible to combine these measures in order to increase the fructokinase-activity.

According to the invention, genetically modified microorganisms are produced, for example by transformation, transduction, conjugation, or a combination of these methods, with a vector containing the desired gene, an allele of this gene or parts thereof, and includes a gene enabling the expression of the vector. The heterologous expression is achieved in particular by integrating the gene or alleles into the chromosome of the cell or an extrachromosomally replicating vector.

In this context it is particularly preferred that the at least one genetic modification A) comprises an overexpression of the rbsK-gene, preferably an overexpression of the rbsK-gene on an episomal plasmid under control of the ackA-promoter. The ackA-promoter preferably comprises a nucleic acid selected from the group consisting of:
a3) nucleic acids having the nucleotide sequence of SEQ ID NO: 7;
b3) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of a3), the identity being the identity over the total length of the nucleic acids of a3).

The extent in which a gene is expressed in a cell can, for example, be determined by means of Real-Time PCR. Details for determining gene expression in a cell can by means of Real-Time PCT are disclosed by Wong and Medrano in "*Real-time PCR for mRNA quantitation*", Bio-Techniques, Vol. 39, No. 1, July 2005, pp. 75-85.

Reduced Phosphotransferase-Activity

According to a particularly preferred embodiment of the genetically modified microorganism that is used in the process according to the present invention the genetically modified microorganism additionally comprises B) at least one genetic modification that leads to a reduced activity of the enzyme encoded by the fruA-gene, compared to the original microorganism that has not been genetically modified. Such a genetic modification can, for example, be a modification of the fruA-gene itself and/or a modification of a regulatory element of the fruA-gene, wherein the modification of the fruA-gene and/or the modification of a regulatory element of the fruA-gene lead/leads to a reduced activity of the enzyme encoded by the fruA-gene, compared to the original microorganism in which the fruA-gene and/or the regulatory element of the fruA-gene have/has not been modified.

The reduction of the enzyme activity ($\Delta_{activity}$) is defined as follows:

$$\Delta_{activity} = 100\% - \left(\frac{\text{activity of the genetically modified microorganism}}{\text{activity of the orginal microorganism}} \times 100\%\right)$$

wherein, when determining $\Delta_{activity}$, the activity in the original microorganism and the activity in the genetically modified microorganism are determined under exactly the same conditions. Methods for the detection and determination of the activity of the enzyme that is encoded by the fruA-gene can be found, for example, in the above mentioned publication of Helanto et al.

The reduced activity of the fructose-specific phosphotransferase encoded by the fruA-gene (or, as described later, "a reduced lactate dehydrogenase activity" or "a reduced pyruvate formate lyase activity") can be a reduction of the enzymatic activity by at least 50%, compared to the activity of said enzyme in the original cell, or a reduction of the enzymatic activity by at least 90%, or more preferably a reduction of the enzymatic activity by at least 95%, or more preferably a reduction of the enzymatic activity by at least 98%, or even more preferably a reduction of the enzymatic activity by at least 99% or even more preferably a reduction of the enzymatic activity by at least 99.9%. The term "a reduced activity of the fructose-specific phosphotransferase" or—as described below—"a reduced lactate dehydrogenase activity" or "a reduced pyruvate formate lyase activity", also encompasses a modified microorganism which has no detectable activity of these enzymes.

A reduced phosphotransferase-activity can be accomplished by a genetic modification of the fruA-gene itself. In this context it is particularly preferred that genetic modification B) comprises an inactivation of the fruA-gene, wherein this inactivation is preferably accomplished by a deletion of the fruA-gene or parts thereof. It is also possible to use a gene or allele which codes for a corresponding enzyme having a reduced activity or by introducing one or more gene mutations which lead to a reduced activity of phosphotransferase. Such mutations can again be generated undirected either by classical methods, such as evolutionary adoption, UV irradiation or mutagenic chemicals, or targeted by genetic engineering methods such as deletion (s), insertion (s) and/or nucleotide exchange(s) by side directed mutagensis. Also, a reduced phosphotransferase-activity can be accomplished by a modifying regulatory elements of the fruA-gene, such as regulatory sequences or sites associated with expression of the fruA-gene (e.g., by removing strong promoters or repressible promoters), regulatory proteins, suppressors, enhancers, transcriptional activators and the like involved in transcription of the fruA-gene and/or the translation of the gene product.

According to a preferred embodiment of the genetically modified microorganism used in the process according to the present invention, the inactivation of the fruA-gene is accomplished by a deletion of the fruA-gene or at least a part thereof, a deletion of a regulatory element of the fruA-gene or parts thereof, such as a promotor sequence, or by an introduction of at least one mutation into the fruA-gene.

In the following, a suitable technique for recombination, in particular for introducing a mutation or for deleting sequences, is described.

This technique is also sometimes referred to as the "Campbell recombination" herein (Leenhouts et al., *Appl Env Microbiol*. (1989), Vol. 55, pages 394-400). "Campbell in", as used herein, refers to a transformant of an original host cell in which an entire circular double stranded DNA molecule (for example a plasmid) has integrated into a chromosome by a single homologous recombination event (a cross in event), and that effectively results in the insertion of a linearized version of said circular DNA molecule into a first DNA sequence of the chromosome that is homologous to a first DNA sequence of the said circular DNA molecule. "Campbelled in" refers to the linearized DNA sequence that has been integrated into the chromosome of a "Campbell in" transformant. A "Campbell in" contains a duplication of the first homologous DNA sequence, each copy of which includes and surrounds a copy of the homologous recombination crossover point.

"Campbell out", as used herein, refers to a cell descending from a "Campbell in" transformant, in which a second homologous recombination event (a cross out event) has occurred between a second DNA sequence that is contained on the linearized inserted DNA of the "Campbelled in" DNA, and a second DNA sequence of chromosomal origin, which is homologous to the second DNA sequence of said linearized insert, the second recombination event resulting in the deletion (jettisoning) of a portion of the integrated DNA sequence, but, importantly, also resulting in a portion (this can be as little as a single base) of the integrated Campbelled in DNA remaining in the chromosome, such that compared to the original host cell, the "Campbell out" cell contains one or more intentional changes in the chromosome (for example, a single base substitution, multiple base substitutions, insertion of a heterologous gene or DNA sequence, insertion of an additional copy or copies of a homologous gene or a modified homologous gene, or insertion of a DNA sequence comprising more than one of these aforementioned examples listed above). A "Campbell out" cell is, preferably, obtained by a counter-selection against a gene that is contained in a portion (the portion that is desired to be jettisoned) of the "Campbelled in" DNA sequence, for example the *Bacillus subtilis* sacB-gene, which is lethal when expressed in a cell that is grown in the presence of about 5% to 10% sucrose. Either with or without a counter-selection, a desired "Campbell out" cell can be obtained or identified by screening for the desired cell, using any screenable phenotype, such as, but not limited to, colony morphology, colony color, presence or absence of antibiotic resistance, presence or absence of a given DNA sequence by polymerase chain reaction, presence or absence of an auxotrophy, presence or absence of an enzyme, colony nucleic acid hybridization, antibody screening, etc. The term "Campbell in" and "Campbell out" can also be used as verbs in various tenses to refer to the method or process described above.

It is understood that the homologous recombination events that leads to a "Campbell in" or "Campbell out" can occur over a range of DNA bases within the homologous DNA sequence, and since the homologous sequences will be identical to each other for at least part of this range, it is not usually possible to specify exactly where the crossover event occurred. In other words, it is not possible to specify precisely which sequence was originally from the inserted DNA, and which was originally from the chromosomal DNA. Moreover, the first homologous DNA sequence and the second homologous DNA sequence are usually separated by a region of partial non-homology, and it is this region of non-homology that remains deposited in a chromosome of the "Campbell out" cell.

Preferably, first and second homologous DNA sequence are at least about 200 base pairs in length, and can be up to several thousand base pairs in length. However, the procedure can be made to work with shorter or longer sequences. For example, a length for the first and second homologous sequences can range from about 500 to 2000 bases, and the obtaining of a "Campbell out" from a "Campbell in" is facilitated by arranging the first and second homologous sequences to be approximately the same length, preferably with a difference of less than 200 base pairs and most preferably with the shorter of the two being at least 70% of the length of the longer in base pairs.

The fruA-gene or parts of which that may be deleted by the above mentioned "Campbell recombination" or in which at least one mutation is introduced by the above mentioned "Campbell recombination" preferably comprises a nucleic acid as defined above.

According to a further preferred embodiment of the genetically modified microorganism that is used in the process according to the present invention the microorganism may additionally be characterized by
  a reduced pyruvate formate lyase activity,
  a reduced lactate dehydrogenase activity, and/or
  a reduced pyruvate formate lyase activity and a reduced lactate dehydrogenase activity.

Modified microorganisms being deficient in lactate dehydrogenase and/or being deficient in pyruvate formate lyase activity are disclosed in WO-A-2010/092155, US 2010/0159543 and WO-A-2005/052135, the disclosure of which with respect to the different approaches of reducing the activity of lactate dehydrogenase and/or pyruvate formate lyase in a microorganism, preferably in a bacterial cell of the genus *Pasteurella*, particular preferred in *Basfia succiniciproducens* strain DD1, is incorporated herein by reference. Methods for determining the pyruvate formate lyase activity are, for example, disclosed by Asanum N. and Hino T. in "*Effects of pH and Energy Supply on Activity and Amount of Pyruvate-Formate-Lyase in Streptococcus bovis*", Appl. Environ. Microbiol. (2000), Vol. 66, pages 3773-3777 and methods for determining the lactate dehydrogenase activity are, for example, disclosed by Bergmeyer, H. U., Bergmeyer J. and Grassi, M. (1983-1986) in "*Methods of Enzymatic Analysis*", 3$^{rd}$ Edition, Volume III, pages 126-133, Verlag Chemie, Weinheim In this context it is preferred that the reduction of the activity of lactate dehydrogenase is achieved by an inactivation of the IdhA-gene (which encodes the lactate dehydrogenase; LdhA; EC 1.1.1.27 or EC 1.1.1.28) and the reduction of the pyruvate formate lyase is achieved by an inactivation of the pflA-gene (which encodes for an activator of pyruvate formate lyase; PflA; EC 1.97.1.4) or the pflD-gene (which encodes the pyruvate formate lyase; PflD; EC 2.3.1.54), wherein the inactivation of these genes (i. e. IdhA, pflA and pflD) is preferably achieved by a deletion of theses genes or parts thereof, by a deletion of a regulatory element of these genes or at least a part thereof or by an introduction of at least one mutation into these genes, wherein these modifications are preferably performed by means of the "Campbell recombination" as described above.

The IdhA-gene the activity of which is reduced in the genetically modified microorganism that is used in the process according to the present invention preferably comprises a nucleic acid selected from the group consisting of:
  α1) nucleic acids having the nucleotide sequence of SEQ ID NO: 8;
  α2) nucleic acids encoding the amino acid sequence of SEQ ID NO: 9;
  α3) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of α1) or α2), the identity being the identity over the total length of the nucleic acids of α1) or α2);
  α4) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of α1) or α2), the identity being the identity over the total length of amino acid sequence encoded by the nucleic acids of α1) or α2);
  α5) nucleic acids capable of hybridizing under stringent conditions with a complementary sequence of any of the nucleic acids according to α1) or α2); and
  α6) nucleic acids encoding the same protein as any of the nucleic acids of α1) or α2), but differing from the nucleic acids of α1) or α2) above due to the degeneracy of the genetic code.

The pflA-gene the activity of which is reduced in the genetically modified microorganism that is used in the process according to the present invention preferably comprises a nucleic acid selected from the group consisting of:
  β1) nucleic acids having the nucleotide sequence of SEQ ID NO: 10;
  β2) nucleic acids encoding the amino acid sequence of SEQ ID NO: 11;
  β3) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of β1) or β2), the identity being the identity over the total length of the nucleic acids of β1) or β2);
  β4) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of β1) or β2), the identity being the identity over the total length of amino acid sequence encoded by the nucleic acids of β1) or β2)

β5) nucleic acids capable of hybridizing under stringent conditions with a complementary sequence of any of the nucleic acids according to β1) or β2); and β6) nucleic acids encoding the same protein as any of the nucleic acids of β1) or β2), but differing from the nucleic acids of β1) or β2) above due to the degeneracy of the genetic code.

The pflD-gene the activity of which is reduced in the genetically modified microorganism that is used in the process according to the present invention preferably comprises a nucleic acid selected from the group consisting of:

γ1) nucleic acids having the nucleotide sequence of SEQ ID NO: 12;

γ2) nucleic acids encoding the amino acid sequence of SEQ ID NO: 13;

γ3) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of γ1) or γ2), the identity being the identity over the total length of the nucleic acids of γ1) or γ2);

γ4) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of γ1) or γ2), the identity being the identity over the total length of amino acid sequence encoded by the nucleic acids of γ1) or γ2);

γ5) nucleic acids capable of hybridizing under stringent conditions with a complementary sequence of any of the nucleic acids according to γ1) or γ2); and γ6) nucleic acids encoding the same protein as any of the nucleic acids of γ1) or γ2), but differing from the nucleic acids of γ1) or γ2) above due to the degeneracy of the genetic code.

In this context it is preferred that the modification of the genetically modified microorganism that is used in the process according to the present invention, in addition to the at least one modification A) or in addition to the at least one modification A) and the at least one modification B), further comprises:

C) a deletion of the IdhA-gene or at least a part thereof, a deletion of a regulatory element of the IdhA-gene or at least a part thereof or an introduction of at least one mutation into the IdhA-gene;

D) a deletion of the pflD-gene or at least a part thereof, a deletion of a regulatory element of the pflD-gene or at least a part thereof or an introduction of at least one mutation into the pflD-gene;

E) a deletion of the pflA-gene or at least a part thereof, a deletion of a regulatory element of the pflA-gene or at least a part thereof or an introduction of at least one mutation into the pflA-gene;

F) a deletion of the IdhA-gene or at least a part thereof, a deletion of a regulatory element of the IdhA-gene or at least a part thereof or an introduction of at least one mutation into the IdhA-gene
   and
   a deletion of the pflD-gene or at least a part thereof, a deletion of a regulatory element of the pflD-gene or at least a part thereof or an introduction of at least one mutation into the pflD-gene;
   or G) a deletion of the IdhA-gene or at least a part thereof, a deletion of a regulatory element of the IdhA-gene or at least a part thereof or an introduction of at least one mutation into the IdhA-gene
   and
   a deletion of the pflA-gene or at least a part thereof, a deletion of a regulatory element of the pflA-gene or at least a part thereof or an introduction of at least one mutation into the pflA-gene.

Particular preferred embodiments of the genetically modified microorganisms used in the process according to the present invention are:

modified bacterial cells of the genus *Basfia*, preferably of the species *Basfia succiniciproducens*, most preferably of the species *Basfia succiniciproducens* strain DD1, in which the rbsK-gene is overexpressed (preferably on an episomal plasmid under control of the ackA-promoter), more preferably in which the fruA-gene is inactivated (preferably by a deletion of the fruA-gene or at least a part thereof) and in which the rbsK-gene is overexpressed (preferably on an episomal plasmid under control of the ackA-promoter);

modified bacterial cells of the genus *Basfia*, preferably of the species *Basfia succiniciproducens*, most preferably of the species *Basfia succiniciproducens* strain DD1, in which the rbsK-gene is overexpressed (preferably on an episomal plasmid under control of the ackA-promoter), more preferably in which the fruA-gene is inactivated (preferably by a deletion of the fruA-gene or at least a part thereof) and in which the rbsK-gene is overexpressed (preferably on an episomal plasmid under control of the ackA-promoter), and in which in addition to these genetic modifications the activity of the lactate dehydrogenase is reduced, preferably by a modification of the IdhA-gene, in particular by a deletion of the IdhA-gene having the nucleic acid sequence according to SEQ ID NO: 8 and encoding for LdhA having the amino acid sequence according to SEQ ID NO: 9;

modified bacterial cells of the genus *Basfia*, preferably of the species *Basfia succiniciproducens*, most preferably of the species *Basfia succiniciproducens* strain DD1, in which the rbsK-gene is overexpressed (preferably on an episomal plasmid under control of the ackA-promoter), more preferably in which the fruA-gene is inactivated (preferably by a deletion of the fruA-gene or at least a part thereof) and in which the rbsK-gene is overexpressed (preferably on an episomal plasmid under control of the ackA-promoter), and in which in addition to these genetic modifications the activity of the pyruvate formate lyase is reduced, preferably by a modification of the pflA-gene or the pflD-gene, in particular by a modification of the pflA-gene having the nucleic acid sequence according to SEQ ID NO: 10 and encoding for PflA having the amino acid sequence according to SEQ ID NO: 11 or by a modification of the pflD-gene having the nucleic acid sequence according to SEQ ID NO: 12 and encoding for PflD having the amino acid sequence according to SEQ ID NO: 13;

modified bacterial cells of the genus *Basfia*, preferably of the species *Basfia succiniciproducens*, most preferably of the species *Basfia succiniciproducens* strain DD1, in which the rbsK-gene is overexpressed (preferably on an episomal plasmid under control of the ackA-promoter), more preferably in which the fruA-gene is inactivated (preferably by a deletion of the fruA-gene or at least a part thereof) and in which the rbsK-gene is overexpressed (preferably on an episomal plasmid under control of the ackA-promoter), and in which in addition to these genetic modifications the activity of the lactate dehydrogenase and the pyruvate formate lyase is reduced, preferably by a modification of the IdhA-gene and the pflA-gene, in particular by a modification of the IdhA-gene having the nucleic acid sequence according to SEQ ID NO: 8 and encoding for LdhA having the amino acid sequence according to SEQ ID NO: 9 or by a modification of the pflA-gene having the nucleic acid sequence according to SEQ ID NO: 10 and encoding for PflA having the amino acid sequence according to SEQ ID NO: 11, or a modification of the IdhA-gene and the pflD-gene, in particular by a modification of the IdhA-gene having the nucleic acid sequence according to SEQ ID NO: 8 and encoding for LdhA having the amino acid sequence according to SEQ ID NO: 9 or by a modification of the pflD-gene having the nucleic acid sequence according to SEQ ID NO: 12 and encoding for PflD having the amino acid sequence according to SEQ ID NO: 13.

In process step I) the genetically modified microorganism according to the present invention is cultured in a culture medium comprising sucrose as the assimilable carbon source to allow the modified microorganism to produce the organic compound, thereby obtaining a fermentation broth comprising the organic compound. Preferred organic compounds that can be produced by the process according to the present invention comprise carboxylic acids such as formic acid, lactic acid, propionic acid, 2-hydroxypropionic acid, 3-hydroxypropionic acid, 3-hydroxybutyric acid, acrylic acid, pyruvic acid or salts of these carboxylic acids, dicarboxylic acids such as malonic acid, succinic acid, malic acid, tartaric acid, glutaric acid, itaconic acid, adipic acid or salts thereof, tricarboxylic acids such as citric acid or salts thereof, alcohols such as methanol or ethanol, amino acids such as L-asparagine, L-aspartic acid, L-arginine, L-isoleucine, L-glycine, L-glutamine, L-glutamic acid, L-cysteine, L-serine, L-tyrosine, L-tryptophan, L-threonine, L-valine, L-histidine, L-proline, L-methionine, L-lysine, L-leucine, etc.

According to a preferred embodiment of the process according to the present invention the organic compound is succinic acid. The term "succinic acid", as used in the context of the present invention, has to be understood in its broadest sense and also encompasses salts thereof (i. e. succinate), as for example alkali metal salts, like $Na^+$ and $K^+$-salts, or earth alkali salts, like $Mg^{2+}$ and $Ca^{2+}$-salts, or ammonium salts or anhydrides of succinic acid.

The genetically modified microorganism according to the present invention is, preferably, incubated in the culture medium at a temperature in the range of about 10 to 60° C. or 20 to 50° C. or 30 to 45° C. at a pH of 5.0 to 9.0 or 5.5 to 8.0 or 6.0 to 7.0.

Preferably, the organic compound, especially succinic acid, is produced under anaerobic conditions. Anaerobic conditions may be established by means of conventional techniques, as for example by degassing the constituents of the reaction medium and maintaining anaerobic conditions by introducing carbon dioxide or nitrogen or mixtures thereof and optionally hydrogen at a flow rate of, for example, 0.1 to 1 or 0.2 to 0.5 vvm. Aerobic conditions may be established by means of conventional techniques, as for example by introducing air or oxygen at a flow rate of, for example, 0.1 to 1 or 0.2 to 0.5 vvm. If appropriate, a slight over pressure of 0.1 to 1.5 bar may be applied in the process.

The assimilable carbon source is preferably sucrose. In this context it is preferred that at least 50 wt.-%, preferably at least 75 wt.-%, more preferably at least 90 wt.-%, even more preferably at least 95 wt.-% and most preferably at least 99 wt.-% of the assimilable carbon source, based on the total weight of the assimilable carbon source with the exception of carbon dioxide, is sucrose.

The initial concentration of the assimilable carbon source, preferably the initial concentration of sucrose, is, preferably, adjusted to a value in a range of 5 to 100 g/l, preferably 5 to 75 g/l and more preferably 5 to 50 g/l and may be maintained in said range during cultivation. The pH of the reaction medium may be controlled by addition of suitable bases as for example, gaseous ammonia, $NH_4HCO_3$, $(NH_4)_2CO_3$, NaOH, $Na_2CO_3$, $NaHCO_3$, KOH, $K_2CO_3$, $KHCO_3$, $Mg(OH)_2$, $MgCO_3$, $Mg(HCO_3)_2$, $Ca(OH)_2$, $CaCO_3$, $Ca(HCO_3)_2$, CaO, $CH_6N_2O_2$, $C_2H_7N$ and/or mixtures thereof. These alkaline neutralization agents are especially required if the organic compounds that are formed in the course of the fermentation process are carboxylic acids or dicarboxylic acids. In the case of succinic acid as the organic compound, $Mg(OH)_2$ is a particular preferred base.

The fermentation step I) according to the present invention can, for example, be performed in stirred fermenters, bubble columns and loop reactors. A comprehensive overview of the possible method types including stirrer types and geometric designs can be found in Chmiel: "*Bio-prozesstechnik: Einführung in die Bioverfahrenstechnik*", Volume 1. In the process according to the present invention, typical variants available are the following variants known to those skilled in the art or explained, for example, in Chmiel, Hammes and Bailey: "*Biochemical Engineering*", such as batch, fed-batch, repeated fed-batch or else continuous fermentation with and without recycling of the biomass. Depending on the production strain, sparging with air, oxygen, carbon dioxide, hydrogen, nitrogen or appropriate gas mixtures may be effected in order to achieve good yield (YP/S).

Particularly preferred conditions for producing the organic acid, especially succinic acid, in process step I) are:
Assimilable carbon source: sucrose
Temperature: 30 to 45° C.
pH: 5.5 to 7.0
Supplied gas: $CO_2$ It is furthermore preferred in process step I) that the assimilable carbon source, preferably sucrose, is converted to the organic compound, preferably to succinic acid, with a carbon yield YP/S of at least 0.5 g/g up to about 1.18 g/g; as for example a carbon yield YP/S of at least 0.6 g/g, of at least 0.7 g/g, of at least 0.75 g/g, of at least 0.8 g/g, of at least 0.85 g/g, of at least 0.9 g/g, of at least 0.95 g/g, of at least 1.0 g/g, of at least 1.05 g/g or of at least 1.1 g/g (organic compound/carbon, preferably succinic acid/carbon).

It is furthermore preferred in process step I) that the assimilable carbon source, preferably sucrose, is converted to the organic compound, preferably to succinic acid, with a specific productivity yield of at least 0.6 g/g $DCW^{-1}$ $h^{-1}$ organic compound, preferably succinic acid, or of at least of at least 0.65 g/g $DCW^{-1}$ $h^{-1}$, of at least 0.7 g/g $DCW^{-1}$ $h^{-1}$, of at least 0.75 g/g $DCW^{-1}$ $h^{-1}$ or of at least 0.77 g/g $DCW^{-1}$ $h^{-1}$ organic compound, preferably succinic acid.

It is furthermore preferred in process step I) that the sucrose is converted to the organic compound, preferably to succinic acid, with a space time yield for the organic compound, preferably for succinic acid, of at least 2.2 g/(L×h) or of at least 2.5 g/(L×h), at least 2.75 g/(L×h), at least 3 g/(L×h), at least 3.25 g/(L×h), at least 3.5 g/(L×h), at least 3.7 g/(L×h), at least 4.0 g/(L×h) at least 4.5 g/(L×h) or at least 5.0 g/(L×h) of the organic compound, preferably succinic acid. According to another preferred embodiment of the process according to the present invention in process step I) the genetically modified microorganism is converting at least 20 g/L, more preferably at least 25 g/l and even more preferably at least 30 g/l sucrose to at least 20 g/l, more preferably to at least 25 g/l and even more preferably at least 30 g/l of the organic compound, preferably succinic acid.

The different yield parameters as described herein ("carbon yield" or "YP/S"; "specific productivity yield"; or "space-time-yield (STY)") are well known in the art and are determined as described for example by Song and Lee, 2006. "Carbon yield" and "YP/S" (each expressed in mass of organic compound produced/mass of assimilable carbon source consumed) are herein used as synonyms. The specific productivity yield describes the amount of a product, like succinic acid, that is produced per h and L fermentation broth per g of dry biomass. The amount of dry cell weight stated as "DCW" describes the quantity of biologically active microorganism in a biochemical reaction. The value is given as g product per g DCW per h (i.e. g g $DCW^{-1}$ $h^{-1}$). The space-time-yield (STY) is defined as the ratio of the total amount of organic compound formed in the fermentation process to the volume of the culture, regarded over the entire time of cultivation. The space-time yield is also known as the "volumetric productivity".

In process step II) the organic compound, preferably succinic acid, is recovered from the fermentation broth obtained in process step I).

Usually, the recovery process comprises the step of separating the genetically modified microrganims from the fermentation broth as the so called "biomass". Processes for removing the biomass are known to those skilled in the art, and comprise filtration, sedimentation, flotation or combinations thereof. Consequently, the biomass can be removed, for example, with centrifuges, separators, decanters, filters or in a flotation apparatus. For maximum recovery of the product of value, washing of the biomass is often advisable, for example in the form of a diafiltration. The selection of the method is dependent upon the biomass content in the fermentation broth and the properties of the biomass, and also the interaction of the biomass with the organic compound (e. the product of value). In one embodiment, the fermentation broth can be sterilized or pasteurized. In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

The recovery process may further comprise additional purification steps in which the organic compound, preferably succinic acid, is further purified. If, however, the organic compound is converted into a secondary organic product by chemical reactions as described below, a further purification of the organic compound is, depending on the kind of reaction and the reaction conditions, not necessarily required. For the purification of the organic compound obtained in process step II), preferably for the purification of succinic acid, methods known to the person skilled in the art can be used, as for example crystallization, filtration, electrodialysis and chromatography. In the case of succinic acid as the organic compound, for example, succinic acid may be isolated by precipitating it as a calcium succinate product by using calcium hydroxide, -oxide, -carbonate or hydrogen carbonate for neutralization and filtration of the precipitate. The succinic acid is recovered from the precipitated calcium succinate by acidification with sulfuric acid followed by filtration to remove the calcium sulfate (gypsum) which precipitates. The resulting solution may be further purified by means of ion exchange chromatography in order to remove undesired residual ions. Alternatively, if magnesium hydroxide, magnesium carbonate or mixtures thereof have been used to neutralize the fermentation broth, the fermentation broth obtained in process step I) may be acidified to transform the magnesium succinate contained in the medium into the acid form (i. e. succinic acid), which subsequently can be crystallized by cooling down the acidified medium. Examples of further suitable purification processes are disclosed in EP-A-1 005 562, WO-A-2008/010373, WO-A-2011/082378, WO-A-2011/043443, WO-A-2005/030973, WO-A-2011/123268 and WO-A-2011/064151 and EP-A-2 360 137.

According to a preferred embodiment of the process according to the present invention the process further comprises the process step:
I) conversion of the organic compound contained in the fermentation broth obtained in process step I) or conversion of the recovered organic compound obtained in process step II) into a secondary organic product being different from the organic compound by at least one chemical reaction.

In case of succinic acid as the organic compound preferred secondary organic products are selected from the group consisting of succinic acid esters and polymers thereof, tetrahydrofuran (THF), 1,4-butanediol (BDO), gamma-butyrolactone (GBL) and pyrrolidones.

According to a preferred embodiment for the production of THF, BDO and/or GBL this process comprises:
b1) either the direct catalytic hydrogenation of the succinic acid obtained in process steps I) or II) to THF and/or BDO and/or GBL or
b2) the chemical esterification of succinic acid and/or succinic acid salts obtained in process steps I) or II) into its corresponding di-lower alkyl ester and subsequent catalytic hydrogenation of said ester to THF and/or BDO and/or GBL.

According to a preferred embodiment for the production of pyrrolidones this process comprises:
b) the chemical conversion of succinic acid ammonium salts obtained in process steps I) or II) to pyrrolidones in a manner known per se.

For details of preparing these compounds reference is made to US-A-2010/0159543 and WO-A-2010/092155.

A contribution to solving the problems mentioned at the outset is furthermore provided by a genetically modified microorganism that comprises
A) at least one genetic modification that leads to an increased activity of the enzyme encoded by the rbsK-gene, compared to the original microorganism that has not been genetically modified,
wherein the original microorganism belongs to the family Pasteurellaceae.

Preferred embodiments of the genetically modified microorganisms according to the present invention are those embodiments that have been described above as preferred genetically modified microorganisms to be used in the process according to the present invention.

A contribution to solving the problems mentioned at the outset is furthermore provided by the use of the genetically modified microorganism according to the present invention for the fermentative production of organic compounds, preferably succinic acid, from sucrose as an assimilable carbon source. Preferred organic compounds and preferred conditions for the fermentative production of organic compounds are those compounds and conditions that have already been described in connection with process step I) of the process according to the present invention.

The invention is now explained in more detail with the aid of non-limiting examples.

EXAMPLES

Example 1: Generation of Deletion Constructs

Vector and strain construction were conducted by standard techniques as described previously (Becker et al., Biotechnology and Bioengineering, Vol. 110 (2013), pages 3013-3023). All mutants constructed are listed in Table 1:

TABLE 1

Nomenclature of the DD1-wildtype and mutants referred to in the examples strain wildtype DD1 (deposit DSM18541)
DD1 $P_{ackA}$rbsK
DD1 $\Delta$fruAP$_{ackA}$rbsK Specific primer sequences used for strain construction and validation are given in Table 2:

TABLE 2 primer sequenced used in the examples

| Primer | Sequence 5' → 3' |
|---|---|
| $PR_{fruA}1$ | tgctctagatgcggaagagagcctttccgg (SEQ ID NO: 14) |
| $PR_{fruA}2$ | caccaggttttggctgccgcagtaaaacaatttcctaatcaa gcataaagcctttgtttatctc (SEQ ID NO: 15) |
| $PR_{fruA}3$ | gagataaacaaaggctttatgcttgattaggaaattgtttta ctgcggcagccaaaacctggtg (SEQ ID NO: 16) |
| $PR_{fruA}4$ | ccgctcgagtaggagtaactcaaggtcaccgtttg (SEQ ID NO: 17) |
| $PR_{rbsK}1$ | ggcggccgctctagaccgaatatttctgccccgc (SEQ ID NO: 18) |
| $PR_{rbsK}2$ | gtttgtcatatgcattgaacgaatagacgtttgggaatgtta (SEQ ID NO: 19) |
| $PR_{rbsK}3$ | acgtctattcgttcaatgcatatgacaaacaaaatttgggta ttag (SEQ ID NO: 20) |
| $PR_{rbsK}4$ | gggcccccctcgagcctagcttaaagatagccggtaaa (SEQ ID NO: 21) |

Marker free deletion of fruA, encoding the fructose PTS, used the integrative vector pClik$^{CM}$ (Becker et al., Metabolic Engineering, Vol. 13 (2011), pages 59-168) and the primers $PR_{fruA}1$-$PR_{fruA}4$ (Table 2). The fruA-deletion fragment was ligated into the vector pClik int sacB (Kind et al., Metabolic Engineering, Vol. 12 (2010), pages 341-351) via the restriction sites XbaI and XhoI. Desired elimination of fruA in the genome was verified by PCR. Preparation of ΔfruA Basfia-strains by means of plasmis pSacB_delta_fruA is also disclosed in WO 2015/118051 A1.

For overexpression of fructokinase (rbsK), the episomal plasmid pJFF224 (Frey, Res. Microbiol. Vol. 143 (3) (1992), pages 263-9.1992) was used. The gene was expressed under control of the promoter of ackA, encoding acetate kinase. For seamless fusion of promoter and gene, overlap extension PCR was applied. To this end, the ackA-promoter and the rbsK-gene were first amplified using the primer combination $PR_{rbsK}1$/$PR_{rbsK}2$ and $PR_{rbsK}3$/$PR_{rbsK}4$, respectively. The resulting PCR fragments were then fused to the 1520 bp-sized promoter gene construct with $PR_{rbsK}1$/$PR_{rbsK}4$. Subcloning of the $P_{ackA}$rbsK construct into the XbaI and XhoI digested vector pJFF224 was conducted using the InFusion kit (Clontech Laboratories, Mountain View, Calif., USA) and yielded the plasmid pJFF224_$P_{ackA}$rbsK. Transformation of *B. succiniciproducens* with pJFF224 and pJFF224_$P_{ackA}$rbsK was carried out by electroporation (Becker et al., 2011). The resulting mutants (Table 1) were analyzed by PCR and enzyme activity studies. PCR was routinely performed with proof-reading polymerases (Phusion High-Fidelity PCR Kit, Thermo Fisher Scientific, Schwerte, Germany).

Example 2: Cultivation of DD1, DD1 $P_{ackA}$rbsK and DD1 Δfru AP$_{ackA}$rbsK on Sucrose The productivity of the DD1-strain was compared with the productivity of the mutant strains DD1 $P_{ackA}$rbsK and DD1 ΔfruAP$_{ackA}$rbsK in the presence of sucrose as a carbon source. Productivity was analyzed utilizing media and incubation conditions described below.

1. Medium Preparation

For physiological studies and for succinate production, first pre-cultivation of *B. succiniciproducens* was conducted in complex medium, which contained per liter: 50 g sucrose, 5 g yeast extract (Becton Dickinson, Franklin Lakes, N.J., US), 5 g bacto peptone 144 (Becton Dickinson), 1 g NaCl, 0.2 g $MgCl_2 \cdot 6H_2O$, 0.2 g $CaCl_2 \cdot 2H_2O$, 3 g $K_2HPO_4$, 1 g $(NH_4)_2SO_4$, and 50 g $MgCO_3$. For second pre-cultivation and main cultivation, a minimal medium was used, which contained per liter: 50 g sucrose, 1 g NaCl, 0.2 g $MgCl_2 \cdot 6H_2O$, 0.2 g $CaCl_2 \cdot 2H_2O$, 3 g $K_2HPO_4$, 5 g $(NH_4)_2SO_4$, 3 mg thiamin.HCl, 0.6 mg riboflavin, 3 mg nicotinic acid, 10 mg Ca-pantothenate, 1 mg pyridoxal.HCl, 0.5 mg biotin, 0.05 mg cyanocobalamin, and 50 g $MgCO_3$. Carbon dioxide was applied to the culture bottles (serum flasks) at 0.8 bar overpressure. For cultivation of plasmid containing strains, chloramphenicol was added to a final concentration of 50 µg mL$^{-1}$ to the medium.

For enzyme assays, cells were grown in minimal medium containing per liter: 50 g sucrose, 1 g NaCl, 0.2 g $MgCl_2 \cdot 6H_2O$, 0.2 g $CaCl_2 \cdot 2H_2O$, 3 g $K_2HPO_4$, 5 g $(NH_4)_2SO_4$, 3 mg thiamin.HCl, 0.6 mg riboflavin, 3 mg nicotinic acid, 10 mg Ca-pantothenate, 1 mg pyridoxal.HCl, 0.5 mg biotin and 0.05 mg cyanocobalamin with automated addition of 1 M $Na_2CO_3$ for pH control.

2. Cultivations

For anaerobic cultivation in serum flaks cultivations were conducted in 30 mL serum bottles, equipped with butyl rubber seals for sampling, and filled with 10 mL medium under a $CO_2$ atmosphere at 0.8 bar overpressure. After inoculation from cryo-stocks, the first preculture was incubated for 8 h at 37° C. and at 130 rpm on an orbital shaker. During exponential growth, cells were harvested by centrifugation (3 min, 16,000×g, 16° C.), washed with 1 mL medium and used to inoculate the second pre-culture to an initial optical density ($OD_{600}$) of 0.3. After 10 h of incubation, exponentially growing cells were harvested and washed as described above, and were then used to inoculate the main culture to an initial $OD_{600}$ of 0.08.

3. Analytics

Succinic acid was analyzed by HPLC. Enzyme activity was determined in crude cell-free extracts. For the preparation of crude cell-free extracts, cells were harvested by centrifugation (5 min, 5,000×g, 4° C.), washed with 100 mM Tris.HCl (0.75 mM dithiothreitol, pH 7.8), resuspended in the same buffer to a concentration of 0.33 (g cell wet weight) $mL^{-1}$ and were then disrupted with a bench-top homogenizer (Precellys 24, Peqlab, VWR International GmbH, Darmstadt, Germany). Enzyme activities were quantified spectrophotometrically (Spectronic Helios, Thermo Electron Corporation, Waltham, Mass., 255 USA) at 37° C. Fructokinase was assayed as described by Helanto et al. 2006) in 100 mM Tris.HCl (pH 7.8, 10 mM $MgCl_2$), 1 U $mL^{-1}$ glucose 6-phosphate dehydrogenase, 2 U $mL^{-1}$ phosphoglucoisomerase, 1 mM $NADP^+$ and different concentrations of ATP (0-5 mM) and fructose (0-25 mM) for determination of kinetic parameters.

4. Results

The results of the ezmyne assay for the determination of the activity of fructokinase in strains DD1, DD1 $P_{ackA}$rbsK and DD1 $\Delta$fruAP$_{ackA}$rbsK is shown in table 3:

TABLE 3

| strain | specific fructokinase activity |
|---|---|
| | specific activity [mU/mg] |
| DD1 | 67 ± 3 |
| DD1 $P_{ackA}$rbsK | 200 ± 3 |
| DD1 $\Delta$fruAP$_{ackA}$rbsK | 154 ± 3 |

Table 4 shows the formation of succinic acid from sucrose as the sole carbon source when the cells are cultured in a batch process:

| strain | mole succinic acid per mole sucrose |
|---|---|
| DD1 | 1.01 ± 0.01 |
| DD1 $P_{ackA}$rbsK | 1.42 ± 0.01 |
| DD1 $\Delta$fruAP$_{ackA}$rbsK | 1.97 ± 0.02 |

SEQUENCES
(nucleotide sequence of 16 S rDNA of strain DD1)

SEQ ID NO: 1 tttgatcctggctcagattgaacgctggcggcaggcttaacacatgcaagtcgaacggtagcgggaggaaagcttgctttctttgccga cgagtggcggacgggtgagtaatgcttggggatctggcttatggaggggggataacgacgggaaactgtcgctaataccgcgtaatat cttcggattaaagggtgggactttcgggccacccgccataagatgagcccaagtgggattaggtagttggtggggtaaaggcctacc aagccgacgatctctagctggtctgagaggatgaccagccacactggaactgagacacggtccagactcctacgggaggcagca gtggggaatattgcacaatgggggaaccctgatgcagccatgccgcgtgaatgaagaaggccttcgggttgtaaagttctttcggtg acgaggaaggtgtttgttttaataggacaagcaattgacgttaatcacagaagaagcaccggctaactccgtgccagcagccgcggt aatacggagggtgcgagcgttaatcggaataactgggcgtaaagggcatgcaggcggacttttaagtgagatgtgaaagcccgg gcttaacctgggaattgcatttcagactgggagtctagagtactttagggaggggtagaattccacgtgtagcggtgaaatgcgtagag atgtggaggaataccgaaggcgaaggcagccccttgggaagatactgacgctcatatgcgaaagcgtggggagcaaacaggatt agataccctggtagtccacgcggtaaacgctgtcgatttggggattgggctttaggcctggtgctcgtagctaacgtgataaatcgacc gcctggggagtacggccgcaaggttaaaactcaaatgaattgacggggccgcacaagcggtggagcatgtggtttaattcgatg caacgcgaagaaccttacctactcttgacatccagagaatcctgtagagatacgggagtgccttcgggagctctgagacaggtgctg catggctgtcgtcagctcgtgttgtgaaatgttgggttaagtcccgcaacgagcgcaacccttatcctttgttgccagcatgtaaagatgg gaactcaaaggagactgccggtgacaaaccggaggaaggtgggatgacgtcaagtcatcatggcccttacgagtagggctaca cacgtgctacaatggtgcatacagagggcggcgataccgcgaggtagagcgaatctcagaaagtgcatcgtagtccggattggagt ctgcaactcgactccatgaagtcggaatcgctagtaatcgcaaatcagaatgttgcggtgaatacgttcccgggccttgtacacaccg cccgtcacaccatgggagtgggttgtaccagaagtagatagcttaaccttcgggggggcgtttaccacggtatgattcatgactggg gtgaagtcgtaacaaggtaaccgtaggggaacctgcgg (nucleotide sequence of 23 S rDNA of strain DD1)

SEQ ID NO: 2 agtaataacgaacgacacaggtataagaatacttgaggttgtatggttaagtgactaagcgtacaaggtggatgccttggcaatcaga ggcgaagaaggacgtgctaatctgcgaaaagcttgggtgagttgataagaagcgtctaacccaagatatccgaatggggcaaccc agtagatgaagaatctactatcaataaccgaatccataggttattgaggcaaaccgggagaactgaaacatctaagtaccccgagg aaaagaaatcaaccgagattacgtcagtagcggcgagcgaaagcgtaagagccggcaagtgatagcatgaggattagaggaat -continued

```
cggctgggaagccgggcggcacagggtgatagccccgtacttgaaaatcattgtgtggtactgagcttgcgagaagtagggcggga
cacgagaaatcctgtttgaagaagggggaccatcctccaaggctaaatactcctgattgaccgatagtgaaccagtactgtgaagg
aaaggcgaaaagaacccggtgaggggagtgaaatagaacctgaaaccttgtacgtacaagcagtgggagcccgcgagggtga
ctgcgtacctttgtataatgggtcagcgacttatattatgtagcgaggttaaccgaatagggagccgaagggaaaccgagtcttaact
gggcgtcgagttgcatgatatagacccgaaacccggtgatctagccatgggcaggttgaaggttgggtaacactaactggaggacc
gaaccgactaatgttgaaaaattagcggatgacctgtggctgggggtgaaaggccaatcaaaccgggagatagctggttctccccg
aaatctatttaggtagagccttatgtgaataccttcgggggtagagcactgtttcggctaggggccatcccggcttaccaacccgatgc
aaactgcgaataccgaagagtaatgcataggagacacacggcgggtgctaacgttcgtcgtggagagggaaacaacccagacc
gccagctaaggtcccaaagtttatattaagtgggaaacgaagtgggaaggcttagacagctaggatgttggcttagaagcagccatc
atttaaagaaagcgtaatagctcactagtcgagtcggcctgcgcggaagatgtaacggggctcaaatatagcaccgaagctgcggc
atcaggcgtaagcctgttgggtaggggagcgtcgtgtaagcggaagaagtggttcgagagggctgctggacgtatcacgagtgcg
aatgctgacataagtaacgataaaacgggtgaaaaacccgttcgccggaagaccaagggttcctgtccaacgttaatcggggcag
ggtgagtcggcccctaaggcgaggctgaagagcgtagtcgatgggaaacgggttaatattcccgtacttgttataattgcgatgtggg
gacggagtaggttaggttatcgacctgttggaaaaggtcgtttaagttggtaggtggagcgtttaggcaaatccggacgcttatcaaca
ccgagagatgatgacgaggcgctaaggtgccgaagtaaccgataccacacttccaggaaaagccactaagcgtcagattataata
aaccgtactataaaccgacacaggtggtcaggtagagaatactcaggcgcttgagagaactcgggtgaaggaactaggcaaaata
gcaccgtaacttcgggagaaggtgcgccggctagattgtagaggtatacccttgaaggttgaaccggtcgaagtgaccgctggct
gcaactgtttattaaaaacacagcactctgcaaacacgaaagtggacgtatagggtgtgatgcctgcccggtgctggaaggttaattg
atggcgttatcgcaagagaagcgcctgatcgaagccccagtaaacgcggccgtaactataacggtcctaaggtagcgaaattcctt
gtcgggtaagttccgacctgcacgaatggcataatgatggccaggctgtctccacccgagactcagtgaaattgaaatcgccgtgaa
gatgcggtgtacccgcggctagacggaaagacccccgtgaacctttactatagcttgacactgaaccttgaattttgatgtgtaggatag
gtgggaggctttgaagcggtaacgccagttatcgtggagccatccttgaaataccacccttttaacgtttgatgttctaacgaagtgcccg
gaacgggtactcggacagtgtctggtgggtagtttgactggggcggtctcctcccaaagagtaacgaggagcacgaaggtttgcta
atgacggtcggacatcgtcaggttagtgcaatggtataagcaagcttaactgcgagacggacaagtcgagcaggtgcgaaagcag
gtcatagtgatccggtggttctgaatggaagggccatcgctcaacgatataaaaggtactccggggataacaggctgataccgccca
agagttcatatcgacggcggtgtttggcacctcgatgtcggctcatcacatcctggggctgaagtaggtcccaagggtatggctgttcgc
catttaaagtggtacgcgagctgggtttaaaacgtcgtgagacagtttggtccctatctgccgtgggcgttggagaattgagagggct
gctcctagtacgagaggaccggagtggacgcatcactggtgttccggttgtgtcgccagacgcattgccgggtagctacatgcgaa
gagataagtgctgaaagcatctcaagcacgaaacttgcctcgagatgagttctcccagtatttaatactgtaagggttgttggagacgac
gacgtagataggccgggtgtgtaagcgttgcgagacgttgagctaaccggtactaattgcccgagaggcttagccatacaacgctca
agtgtttttggtagtgaaagttattacggaataagtaagtagtcagggaatcggct
```

(nucleotide sequence of rbsK-gene from strain DD1)

SEQ ID NO: 3

```
atgcatatgacaaacaaaatttgggtattaggcgatgccgtggtggatttaattcctgacggagacaaccattatttgcgttgcgcaggc
ggcgcaccggctaatgtggcggtcggcgttgcccgtttaggtgtgcctagcgcatttatcggccgtgtaggtaaagatccgttagggga
atttatgcgcgatacgctgaatcaggaaaatgtaaacaccgattatatgttgttagatcctaaacaacgtacttcgacggtggtggttgg
attaaccgacggcgaacgtagttttaccttttatggtgaatccaagtgcggatcaattttttacaaatttccgatctgccgcaatttcaagccg
gagactggttgcactgctgctctatcgccttaatcaatgaaccgacccgcagcgctactttcacggcaatgaaaaatatccgtgcggcc
ggcggtaaagtatctttcgatccgaatttacgcgaaagcttatgaaatcccaggatgaaatgatcgatgtggtgatggaagcggtaa
gccttgccgacgtattgaaattttcagaagaagaattaacgctgttaacccataccgacagcctggaaaatcttttgaaaaaatcacc
gcactttatcccgataaattgattattgtcactttagggaaagatggcgcgctctatcatctgcacggtaaaaagaggtggttgcaggg
aaagcgctgaaaccggtagataccaccggtgccggcgacgcttttgtcagcgggttattagccggattatcacaaacggaaaactgg
```

-continued cagcaacctgaacaactcgttactattattcgccaggccaacgccagcggcgcgcttgccacaacggcaaaaggcgctatgtcggc attaccgaatcggcaacaattagcggaattttttagcaaactaa (amino acid sequence of RbsK from strain DD1)

SEQ ID NO: 4

MHMTNKIWVLGDAVVDLIPDGDNHYLRCAGGAPANVAVGVARLGVPSAFIGRVGKDPLGEFM

RDTLNQENVNTDYMLLDPKQRTSTVVVGLTDGERSFTFMVNPSADQFLQISDLPQFQAGDWL

HCCSIALINEPTRSATFTAMKNIRAAGGKVSFDPNLRESLWKSQDEMIDVVMEAVSLADVLKFS

EEELTLLTHTDSLEKSFEKITALYPDKLIIVTLGKDGALYHLHGKKEVVAGKALKPVDTTGAGDAF

VSGLLAGLSQTENWQQPEQLVTIIRQANASGALATTAKGAMSALPNRQQLAEFLAN (nucleotide sequence of fruA-gene from strain DD1)

SEQ ID NO: 5 ttgaaggataagccgatgaatattttttcttacgcaatcaccaaatttaggtcgtgcaaaagcgttttttattgcaccaggttttggctgccgca gtaaaacaacaaaatcatcaactggtagaaaatgccgaacaagcggatttagcgattgttttcggtaaaactttgccgaatttgaccgc acttttaggtaaaaaagtgtatttggcggatgaagaacaagcgttgaatgcgcctgaaaataccgtcgcgcaggcattaaccgaggct gtggattatgttcaaccggcgcaacaggacgtgcaacccgcaactgcttccggtatgaaaaatatcgtggcggttaccgcttgtccga ccggggtggcgcacaccttatgtctgccgaggcgattacaacctactgccaacagcaaggttggaatgtaaaagtggaaaccaga ggtcaagtcggtgcgaacaatattatttctgcggaagatgtggcggcggccgatttagtctttatcgctacggatattaatgtggatttaag caaattcaaaggaaaaccgatgtatcgtacttcaacgggcttagcattgaagaaaaccgcacaggaatttgataaagcctttaaaga agcgacgatttatcagggtgaagaaactacaaccaccacagaaacacaaacttcaggcgagaaaaaaggtgtatataaacatctt atgaccgggttccccatatgttaccgcttgtcgttgccggcggtttattgattgctatttcgtttatgttcggtattgaggcgtttaaagacgaa aacatcgcaggcggcttgccgaaagcattaatggatatcggcggcggtgcggcgttccacttaatgattgccgtatttgcaggttatgtt gcattctctattgcagaccgtccggggttagccgtaggtcttatcggcggtatgcttgccacatccgccggtgccggtattttgggcggtat tatcgcgggttttcttgccggttatgtagtgaaattcctgaatgatgccattcaactgccagccagtttaacttcgttaaaaccgatttaattc tgcctttattaggttcggcgatcgtcggcttggccatgatttatttattaaatccaccggttgctgcggcaatgaatgcgctaaccgaatggt taaaaggtttgggctcggcaaacgcgctggtgttgggtgcgattcttggcggtatgatgtgtatcgatatgggcggtccggtaaacaaa gccgcttatgtattcggtacgggcatgattggttcacaggtttatacgccgatggctgcggtaatggctgcgggtatggtaccgcctttag gaatggcgattgccacctggattgcgcgcgctaaatttaacgcaagccaacgtgatgcgggtaaagcttcattcgtactaggtttatgct ttatttccgaaggtgcgttaccgtttgttgccgccgaccctgtacgcgtgattgtttcaagtgtaattggcggagccattgccggcgcaattt ctatgagccttgccattacgctgcaagcgcctcacggcggtttattcgtgattccgtttgtgtcgcaaccgttaatgtatttgggtgcgattgc cgtaggcgccttaacaaccggcgttctttacgcaattatcaaaccgaaacaagctgcggaataa (amino acid sequence of FruA from strain DD1)

SEQ ID NO: 6

MKDKPMNIFLTQSPNLGRAKAFLLHQVLAAAVKQQNHQLVENAEQADLAIVFGKTLPNLTALLG

KKVYLADEEQALNAPENTVAQALTEAVDYVQPAQQDVQPATASGMKNIVAVTACPTGVAHTF

MSAEAITTYCQQQGWNVKVETRGQVGANNIISAEDVAAADLVFIATDINVDLSKFKGKPMYRTS

TGLALKKTAQEFDKAFKEATIYQGEETTTTTETQTSGEKKGVYKHLMTGVSHMLPLVVAGGLLI

AISFMFGIEAFKDENIAGGLPKALMDIGGGAAFHLMIAVFAGYVAFSIADRPGLAVGLIGGMLATS

AGAGILGGIIAGFLAGYVVKFLNDAIQLPASLTSLKPILILPLLGSAIVGLAMIYLLNPPVAAAMNAL

TEWLKGLGSANALVLGAILGGMMCIDMGGPVNKAAYVFGTGMIGSQVYTPMAAVMAAGMVPP

LGMAIATWIARAKFNASQRDAGKASFVLGLCFISEGALPFVAADPVRVIVSSVIGGAIAGAISMSL

AITLQAPHGGLFVIPFVSQPLMYLGAIAVGALTTGVLYAIIKPKQAAE (nucleotide sequence of ackA-promoter from strain DD1)

SEQ ID NO: 7 ccgaatatttctgccccgccgatatagtttaaaaaatcccatttttaaatccttaatttatatttcttcaaattttttactactgacttattttaaattt gctgccatttttatcctgtttttaaagatcgcttatcgcatgaaactcaaatggcttattggatatatgtcctaaaaattgaacatttttataacattt tgctaaaaattcaattttttttgacttaaatcgcttttttcagaacttcataatttattttattccgttaaacgtgtatccttattatcggtaacattccc aaacgtctattcgttca (nucleotide sequence of ldhA-gene from strain DD1)

SEQ ID NO: 8 ttgacaaaatcagtatgtttaaataaggagctaactatgaaagttgccgtttacagtactaaaaattatgatcgcaaacatctggatttgg cgaataaaaaatttaattttgagcttcatttctttgattttttacttgatgaacaaaccgcgaaaatggcggagggcgccgatgccgtctgta ttttcgtcaatgatgatgcgagccgcccggtgttaacaaagttggcgcaaatcggagtgaaaattatcgctttacgttgtgccggttttaat aatgtggatttggaggcggcaaaagagctgggattaaaagtcgtacgggtgcctgcgtattcgccggaagccgttgccgagcatgcg atcggattaatgctgactttaaaaccgccgtatccataaggcttatcagcgtacccgcgatgcgaattttctctggaaggattggtcggtttt aatatgttcggcaaaaccgccggagtgattggtacgggaaaaatcggcttggcggctattcgcattttaaaaggcttcggtatggacgtt ctggcgtttgatccttttaaaaatccggcggcggaagcgttgggcgcaaaatatgtcggtttagacgagctttatgcaaaatcccatgtta tcactttgcattgcccggctacggcggataattatcatttattaaatgaagcggcttttaataaaaatgcgcgacggtgtaatgattattaata ccagccgcggcgttttaattgacagccgggcggcaatcgaagcgttaaaacggcagaaaatcggcgctctcggtatggatgtttatg aaaatgaacgggatttgttttttcgaggataaaatctaacgatgttattacggatgatgtattccgtcgcctttcttcctgtcataatgtgcttttttac cggtcatcaggcgttttaacggaagaagcgctgaataatatcgccgatgtgactttatcgaatattcaggcggtttccaaaaatgcaac gtgcgaaaatagcgttgaaggctaa (amino acid sequence of LdhA from strain DD1)

SEQ ID NO: 9

MTKSVCLNKELTMKVAVYSTKNYDRKHLDLANKKFNFELHFFDFLLDEQTAKMAEGADAVCIFV

NDDASRPVLTKLAQIGVKIIALRCAGFNNVDLEAAKELGLKVVRVPAYSPEAVAEHAIGLMLTLN

RRIHKAYQRTRDANFSLEGLVGFNMFGKTAGVIGTGKIGLAAIRILKGFGMDVLAFDPFKNPAAE

ALGAKYVGLDELYAKSHVITLHCPATADNYHLLNEAAFNKMRDGVMIINTSRGVLIDSRAAIEAL

KRQKIGALGMDVYENERDLFFEDKSNDVITDDVFRRLSSCHNVLFTGHQAFLTEEALNNIADVT

LSNIQAVSKNATCENSVEG (nucleotide sequence of pflA-gene from strain DD1)

SEQ ID NO: 10 atgtcggttttaggacgaattcattcatttgaaacctgcgggacagttgacgggccgggaatccgctttatttttattttttacaaggctgcttaa tgcgttgtaaatactgccataatagagacacctgggatttgcacggcggtaaagaaatttccgttgaagaattaatgaaagaagtggtg acctatcgccatttttatgaacgcctcgggcggcggagttaccgcttccggcggtgaagctattttacaggcggaatttgtacgggactgg ttcagagcctgccataaagaaggaattaatacttgcttggataccaacggtttcgtccgtcatcatgatcatattattgatgaattgattgat gacacggatcttgtgttgcttgacctgaaagaaatgaatgaacgggttcacgaaagcctgattggcgtgccgaataaaagagtgctcg aattcgcaaaatatttagcggatcgaaatcagcgtacctggatccgccatgttgtagtgccgggttatacagatagtgacgaagatttgc acatgctggggaatttcattaaagatatgaagaatatcgaaaaagtggaattattaccttatcaccgtctaggcgcccataaatgggaa gtactcggcgataaatacgagcttgaagatgtaaaaccgccgacaaaagaattaatggagcatgttaaggggttgcttgcaggctac gggcttaatgtgacatattag (amino acid sequence of PflA from strain DD1)

SEQ ID NO: 11

MSVLGRIHSFETCGTVDGPGIRFILFLQGCLMRCKYCHNRDTWDLHGGKEISVEELMKEVVTY

RHFMNASGGGVTASGGEAILQAEFVRDWFRACHKEGINTCLDTNGFVRHHDHIIDELIDDTDLV

LLDLKEMNERVHESLIGVPNKRVLEFAKYLADRNQRTWIRHVVVPGYTDSDEDLHMLGNFIKD

MKNIEKVELLPYHRLGAHKWEVLGDKYELEDVKPPTKELMEHVKGLLAGYGLNVTY

-continued (nucleotide sequence of pflD-gene from strain DD1)

SEQ ID NO: 12 atggctgaattaacagaagctcaaaaaaaagcatgggaaggattcgttcccggtgaatggcaaaacggcgtaaatttacgtgactttatccaaaaaaactatactccgtatgaaggtgacgaatcattcttagctgatgcgactcctgcaaccagcgagttgtggaacagcgtgatggaaggcatcaaaatcgaaaacaaaactcacgcacctttagatttcgacgaacatactccgtcaactatcacttctcacaagcctggttatatcaataaagatttagaaaaaatcgttggtcttcaaacagacgctccgttaaaacgtgcaattatgccgtacggcggtatcaaaatgatcaaaggttcttgcgaagtttacggtcgtaaattagatccgcaagtagaatttattttcaccgaatatcgtaaaacccataaccaaggcgtattcgacgtttatacgccggatattttacgctgccgtaaatcaggcgtgttaaccggtttaccggatgcttacggtcgtggtcgtattatcggtgactaccgtcgtttagcggtatacgtattgattacctgatgaaagataaaaaagcccaattcgattcattacaaccgcgtttggaagcgggcgaagacattcaggcaactatccaattacgtgaagaaattgccgaacaacaccgcgctttaggcaaaatcaaagaaatggcggcatcttacggttacgacatttccggccctgcgacaaacgcacaggaagcaatccaatggacatattttgcttatctggcagcggttaaatcacaaaacggtgcggcaatgtcattcggtcgtacgtctacattcttagatatctatatcgaacgtgacttaaaacgcggtttaatcactgaacaacaggcgcaggaattaatggaccacttagtaatgaaattacgtatggttcgtttcttacgtacgccggaatacgatcaattattctcaggcgacccgatgtgggcaaccgaaactatcgccggtatgggcttagacggtcgtccgttggtaactaaaaacagcttccgcgtattacatactttatacactatgggtacttctccggaaccaaacttaactattctttggtccgaacaattacctgaagcgttcaaacgtttctgtgcgaaagtatctattgatacttcctccgtacaatacgaaaatgatgacttaatgcgtcctgacttcaacaacgatgactatgcaatcgcatgctgcgtatcaccgatggtcgtaggtaaacaaatgcaattcttcggtgcgcgcgcaaacttagctaaaactatgttatacgcaattaacggcggtatcgatgagaaaaatggtatgcaagtcggtcctaaaactgcgccgattacagacgaagtattgaatttcgataccgtaatcgaacgtatggacagtttcatggactggttggcgactcaatatgtaaccgcattgaacatcatccacttcatgcacgataaatatgcatatgaagcggcattgatggcgttccacgatcgcgacgtattccgtacaatggcttgcggtatcgcgggtctttccgtggctgcggactcattatccgcaatcaaatatgcgaaagttaaaccgattcgcggcgacatcaaagataaagacggtaatgtcgtggcctcgaatgttgctatcgacttcgaaattgaaggcgaatatccgcaattcggtaacaatgatccgcgtgttgatgatttagcggtagacttagttgaacgtttcatgaaaaaagttcaaaaacacaaaacttaccgcaacgcaactccgacacaatctatcctgactatcacttctaacgtggtatacggtaagaaaccggtaatactccggacggtcgtcgagcaggcgcgccattcggacccggtgcaaacccaatgcacggtcgtgaccaaaaaggtgcggttgcttcacttacttctgtggctaaacttccgttcgcttacgcgaaagacggtatttcatataccttctctatcgtaccgaacgcattaggtaaagatgacgaagcgcaaaaacgcaaccttgccggtttaatggacggttatttccatcatgaagcgacagtggaaggcggtcaacacttgaatgttaacgttcttaaccgtgaaatgttgttagacgcgatggaaaatccggaaaaatacccgcaattaaccattcgtgtttcaggttacgcggttcgtttcaactcattaactaaagagcaacaacaagacgtcatcactcgtacgtttacacaatcaatgtaa (amino acid of PflD from strain DD1)

SEQ ID NO: 13

MAELTEAQKKAWEGFVPGEWQNGVNLRDFIQKNYTPYEGDESFLADATPATSELWNSVMEGI
KIENKTHAPLDFDEHTPSTITSHKPGYINKDLEKIVGLQTDAPLKRAIMPYGGIKMIKGSCEVYGR
KLDPQVEFIFTEYRKTHNQGVFDVYTPDILRCRKSGVLTGLPDAYGRGRIIGDYRRLAVYGIDYL
MKDKKAQFDSLQPRLEAGEDIQATIQLREEIAEQHRALGKIKEMAASYGYDISGPATNAQEAIQ
WTYFAYLAAVKSQNGAAMSFGRTSTFLDIYIERDLKRGLITEQQAQELMDHLVMKLRMVRFLRT
PEYDQLFSGDPMWATETIAGMGLDGRPLVTKNSFRVLHTLYTMGTSPEPNLTILWSEQLPEAF
KRFCAKVSIDTSSVQYENDDLMRPDFNNDDYAIACCVSPMVVGKQMQFFGARANLAKTMLYAI
NGGIDEKNGMQVGPKTAPITDEVLNFDTVIERMDSFMDWLATQYVTALNIIHFMHDKYAYEAAL
MAFHDRDVFRTMACGIAGLSVAADSLSAIKYAKVKPIRGDIKDKDGNVVASNVAIDFEIEGEYPQ
FGNNDPRVDDLAVDLVERFMKKVQKHKTYRNATPTQSILTITSNVVYGKKTGNTPDGRRAGAP
FGPGANPMHGRDQKGAVASLTSVAKLPFAYAKDGISYTFSIVPNALGKDDEAQKRNLAGLMDG
YFHHEATVEGGQHLNVNVLNREMLLDAMENPEKYPQLTIRVSGYAVRFNSLTKEQQQDVITRT
FTQSM

-continued (nucleotide sequence of primer PR$_{fruA}$1)

tgctctagatgcggaagagagcctttccgg

SEQ ID NO: 14

(nucleotide sequence of primer PR$_{fruA}$2)

caccaggttttggctgccgcagtaaaacaatttcctaatcaagcataaagcctttgtttatctc

SEQ ID NO: 15

(nucleotide sequence of primer PR$_{fruA}$3)

gagataaacaaaggctttatgcttgattaggaaattgttttactgcggcagccaaaacctggtg

SEQ ID NO: 16

(nucleotide sequence of primer PR$_{fruA}$4)

ccgctcgagtaggagtaactcaaggtcaccgtttg

SEQ ID NO: 17

(nucleotide sequence of primer PR$_{rbsK}$1)

ggcggccgctctagaccgaatatttctgccccgc

SEQ ID NO: 18

(nucleotide sequence of primer PRr$_{bsK}$2)

gtttgtcatatgcattgaacgaatagacgtttgggaatgtta

SEQ ID NO: 19

(nucleotide sequence of primer PR$_{rbsK}$3)

acgtctattcgttcaatgcatatgacaaacaaaatttgggtattag

SEQ ID NO: 20

(nucleotide sequence of primer PR$_{rbsK}$4)

gggccccccctcgagcctagcttaaagatagccggtaaa

SEQ ID NO: 21

(nucleotide sequence of plasmid pJFF224_P$_{ackA}$rbsK)

ccccggagtggttcgacggcctcaagcgcgccgccgagggccgccgcctgatggtgctggacacgctgcgccggttccacatcga
ggaagaaaacgccagcggccccatgggcccaggtcatcggtcgcatggaggccatcgccgccgataccgggtgctctatcgtgttcc
tgcaccatgccagcaagggcgcggccatgatgggcgcaggcgaccagcagcaggccagccggggcagctcggtactggtcgat
aacatccgctggcagtcctacctgtcgagcatgaccagcgccgaggccgaggaatggggtgtggacgacgaccagcgccggttctt
cgtccgcttcggtgtgagcaaggccaactatggcgcaccgttcgctgatcggtggttcaggcggcatgacggcggggtgctcaagcc
cgccgtgctggagaggcagcgcaagagcaaggggggtgccccgtggtgaagcctaagaacaagcacagcctcagccacgtccg
gcacgacccggcgcactgtctggccccggcctgttccgtgccctcaagcggggcgagcgcaagcgcagcaagctggacgtgac
gtatgactacgcgacggcaagcggatcgagttcagcggcccggagccgctgggcgctgatgatctgcgcatcctgcaagggctg
gtggccatggctgggcctaatggcctagtgcttggcccggaacccaagaccgaaggcggacggcagctccggctgttcctggaacc
caagtgggaggccgtcaccgctgatgccatggtggtcaaaggtagctatcgggcgctggcaaaggaaatcggggcagaggtcgat
agtggtggggcgctcaagcacatacaggactgcatcgagcgccttttggaaggtatccatcatcgcccagaatggccgcaagcggc
aggggttcggctgctgtcggagtacgccagcgacgaggcggacgggcgcctgtacgtgccctgaaccccttgatcgcgcaggcc
gtcatgggtggcggccagcatgtgcgcatcagcatggacgaggtgcgggcgctggacagcgaaaccgcccgcctgctgcaccag
cggctgtgtggctggatcgaccccggcaaaaccggcaaggcttccatagataccttgtgcggctatgtctggccgtcagaggccagt
ggttcgaccatgcgcaagcgccgccagcgggtgcgcgaggcgttgccggagctggtcgcgctgggctggacggtaaccgagttcg
cggcgggcaagtacgacatcacccggcccaaggcggcaggctgaccccccccactctattgtaaacaagacattttttatctttatatt
caatggcttattttcctgctaattggtaataccatgaaaaataccatgctcagaaaaggcttaacaatattttgaaaaattgcctactgagc
gctgccgcacagctccataggccgctttcctggctttgcttccagatgtatgctctcctccggagagtaccgtgactttattttcggcacaa
atacaggggtcgatggataaatacggcgatagtttcctgacggatgatccgtatgtaccggcggaagacaagctgcaaacctgtcag
atggagattgatttaatggcggatgtgctgagagcaccgccccgtgaatccgcagaactgatccgctatgtgtttgcggatgattggcc
ggaataaataaagccgggcttaatacagattaagcccgtatagggtattattactgaataccaaacagcttacggaggacggaatgtt
acccattgagacaaccagactgccttctgattattaatattttcactattaatcagaaggaataaccatgaattttacccggattgacctg
aatacctggaatcgcagggaacactttgccctttatcgtcagcagattaaatgcggattcagcctgaccaccaaactcgatattaccgct -continued

```
ttgcgtaccgcactggcggagacaggttataagttttatccgctgatgatttacctgatctcccgggctgttaatcagtttccggagttccgg
atggcactgaaagacaatgaacttatttactgggaccagtcagaccggtctttactgtctttcataaagaaaccgaaacattctctgca
ctgtcctgccgttattttccggatctcagtgagtttatggcaggttataatgcggtaacggcagaatatcagcatgataccagattgtttccg
cagggaaatttaccggagaatcacctgaatatatcatcattaccgtgggtgagttttgacgggatttaacctgaacatcaccggaaatg
atgattattttgccccggttttacgatggcaaagtttcagcaggaaggtgaccgcgtattattacctgtttctgtacaggttcatcatgcagt
ctgtgatggctttcatgcagcacggtttattaatacacttcagctgatgtgtgataacatactgaaataaattaattaattctgtatttaagcc
accgtatccggcaggaatggtggctttttttttatattttaaccgtaatctgtaatttcgtttcagactggttcaggatcactgtacgataatgcc
cccgcagtttggtaatacccttaataaaaaagaaacagcaaagactgacagcaataataataaagtaagcagtaacaataatatta
acaacaccagatgcagttataataatagtatttaagacaccagaaagactgctgcgacagtcattttgaacaacaccaaaatgccgt
aaaggcagtagtaacaacaccagtgaaaacatcacgatagcatagtgatatgcctgagtgtgtgtaattaaacaataaataaaccg
ccatatataacagaagatagtattctgaatggcatgcttttctgttcagtataaacatatcatcccggttggtataaggatgatatataataa
gttaagctgaacacatatttattttggttttattttacaaataaagtaagacgatccgttaagtcaaagcggggtatatttattataccctgcttt
tttatttgtccgccgggcgcggataatggatcagattatgcagtgtcacaatggccttaccgggattggcgtaagcgtgcgggatatccg
catgaagcgcagggattccccggcagaaacggtgtgccactcatccccagccgcagttgtaatgcgccttccagtacaatgacat
gttctctggttctgaaatccatccctgtcggtgttgcttatgcagtctggtcgggactcggcgtcgtcataattacagccattgcctggttgctt
catgggcaaaagctttatgcttgtaaaccgttttgtgaaaaaattttttaaaataaaaagggggacctctagggtccccaattaattagtaa
tataatctattaaaggtcattcaaaaggtcatccaccggatcccaccgcggtggcggccgctctagaccgaatatttctgccccgccga
tatagttttaaaaaatcccatttttaaatccttaatttatatttcttcaaattttttactactgacttatttttaaatttgctgccatttatcctgttttaaag
atcgcttatcgcatgaaactcaaatggcttattggatatatgtcctaaaaattgaacattttttataacatttgctaaaaattcaatttttttttgac
ttaaatcgctttttttcagaacttcataatttattttattccgttaaacgtgtatccttattatcggtaacattcccaaacgtctattcgttcaatgcat
atgacaaacaaatttgggtattaggcgatgccgtggtggatttaattcctgacggagacaaccattatttgcgttgcgcaggcggcgc
accggctaatgtggcggtcggcgttgcccgtttaggtgtgcctagcgcatttatcggccgtgtaggtaaagatccgttaggggaatttatg
cgcgatacgctgaatcaggaaaatgtaaacaccgattatatgttgttagatcctaaacaacgtacttcgacggtggtggttggattaacc
gacggcgaacgtagttttacctttatggtgaatccaagtgcggatcaattttttacaaatttccgatctgccgcaatttcaagccggagact
ggttgcactgctgctctatcgccttaatcaatgaaccgaccgcagcgctactttcacggcaatgaaaaatatccgtgcggccggcggt
aaagtatctttcgatccgaatttacgcgaaagcttatggaaatcccaggatgaaatgatcgatgtggtgatggaagcggtaagccttgc
cgacgtattgaaattttcagaagaagaattaacgctgttaacccataccgacagcctggaaaaatctttttgaaaaaatcaccgcacttt
atcccgataaattgattattgtcactttagggaaagatggcgcgctctatcatctgcacggtaaaaaagaggtggttgcagggaaagc
gctgaaaccggtagataccaccggtgccggcgacgcttttgtcagcgggttattagccggattatcacaaacggaaaactggcagca
acctgaacaactcgttactattattcgccaggccaacgccagcggcgcgcttgccacaacggcaaaaggcgctatgtcggcattacc
gaatcggcaacaattagcggaattttttagcaaactaaaattcgcaaatttattccaaactcattctccgattattaattgcatcaacttaa
aaagtaaaaatgcagtgcgttaagcggcctatgtgagtgttccgctaaatctgcacgaattaaagaacgtttatatgcccctaatcggc
aggttatatccattgattagtacagtacaaaaaagtccggcgcttatcaccggacttttttatgcctaaaaatagaatttggtataaatatat
tgtttttttatatttaccggctatcttaagctaggctcgagggggggcccggatcccagtagatttacgtttaaacattttttatttccttttttaattt
aatttaattaacagttggtgctatgacactttacctcatagctggcataattcgcaatactctgggtcttcgagaggtatccaacctgagttg
aaatactttaccatcgatttagcagttgtatcagttatttatattaccttaactcttcgccatccaggagttttaccgtacagattagaggat
aataataacacataattctcgtaagcaatatgagataatttccaagactctatattagctcgtgatgttttccaaggtctaaatcgtcacg
gttcatataattagccaatctcatatgctctctaacttccgatgataagctgtcaaacatgagaattaacgatctgatagagaagggtttgc
tcgggtcggtggctctggtaacgaccagtatcccgatcccggctggccgtcctggccgccacatgaggcatgttccgcgtccttgcaat
actgtgtttacatacagtctatcgcttagcggaaagttctttttaccctcagccgaaatgcctgccgttgctagacattgccagccagtgccc
gtcactcccgtactaactgtcacgaacccctgcaataactgtcacgcccctgcaataactgtcacgaaccctgcaataactgtcac
```

-continued

```
gcccccaaacctgcaaacccagcaggggcgggggctggcggggtgttggaaaaatccatccatgattatctaagaataatccacta ggcgcggttatcagcgcccttgtggggcgctgctgcccttgcccaatatgcccggccagaggccggatagctggtctattcgctgcgct aggctacacaccgccccaccgctgcgcggcaggggaaaggcgggcaaagcccgctaaaccccacaccaaaccccgcagaa atacgctgggagcgcttttagccgctttagcggccttttcccctacccgaagggtggggcgcgtgtgcagcccgcagggcctgtctc ggtcgatcattcagcccggctcatccttctggcgtggcggcagaccgaacaaggcgcggtcgtggtcgcgttcaaggtacgcatccat tgccgccatgagccgatcctccggccactcgctgctgttcaccttggccaaaatcatggcccccaccagcaccttgcgccttgtttcgttc ttgcgctattgctgctgttcccttgcccgcacccgctgaatttcggcattgattcgcgctcgttgttcttcgagcttggccagccgatccgccg ccttgttgctccccttaaccatcttgacaccccattgttaatgtgctgtctcgtaggctatcatggaggcacagcggcggcaatcccgacc ctactttgtaggggagggccattgcatggagccgaaaagcaaaagcaacagcgaggcagcatggcgatttatcaccttacggcga aaaccggcagcaggtcgggcggccaatcggccagggccaaggccgactacatccagcgcgaaggcaagtatgcccgcgacat ggatgaagtcttgcacgccgaatccgggcacatgccggagttcgtcgagcggcccgccgactactgggatgctgccgacctgtatga acgcgccaatgggcggctgttcaaggaggtcgaatttgccctgccggtcgagctgacccctcgaccagcagaaggcgctggcgtccg agttcgcccagcacctgaccggtgccgagcgcctgccgtatacgctggccatccatgccggtggcggcgagaacccgcactgcca cctgatgatctccgagcggatcaatgacggcatcgagcggcccgccgctcagtggttcaagcggtacaacggcaagaccccggag aagggcggggcacagaagaccgaagcgctcaagcccaaggcatggcttgagcagacccgcgaggcatgggccgaccatgcc aaccgggcattagagcgggctggccacgacgcccgcattgaccacagaacacttgaggcgcagggcatcgagcgcctgcccggt gttcacctggggccgaacgtggtggagatggaaggccggggcatccgcaccgacccgggcagacgtggccctgaacatcgacacc gccaacgcccagatcatcgacttacaggaataccgggaggcaatagaccatgaacgcaatcgacagagtgaagaaatccagag xxxxxxgcatcaacgagttagcggagcagatcgaaccgctggcccagagcatggcgacactggccgacgaagcccggcaggtcatgagc cagacccagcaggccagcgaggcgcaggcggcggagtggctgaaagcccagcgccagacaggggcggcatggggtggagctg gccaaagagttgcgggaggtagccgccgaggtgagcagcgccgcgcagagcgcccggagcgcgtcgcgggggtggcactgga agctatggctaaccgtgatgctggcttccatgatgcctacggtggtgctgctgatcgcatcgttgctcttgctcgacctgacgccactgac aaccgaggacggctcgatctggctgcgcttggtggcccgatgaagaacgacaggactttgcaggccataggccgacagctcaagg ccatgggctgtgagcgcttcgatatcggcgtcagggacgccaccaccggccagatgatgaacccgggaatggtcagccgccgaagt gctccagaacacgccatggctcaagcggatgaatgcccagggcaatgacgtgtatatcaggcccgccgagcaggagcggcatgg tctggtgctggtggacgacctcagcgagtttgacctggatgacatgaaagccgagggccgggagcctgccctggtagtggaaacca gcccgaagaactatcaggcatgggtcaaggtggccgacgccgcaggcggtgaacttcgggggcagattgcccggacgctggcca gcgagtacgacgccgacccggccagcgccgacagccgccactatggccgcttggcgggcttcaccaaccgcaaggacaagcac accacccgcgccggttatcagccgtgggtgctgctgcgtgaatccaagggcaagaccgccaccgctggcccggcgctggtgcagc aggctggccagcagatcgagcaggcccagcggcagcaggagaaggcccgcaggctggccagcctcgaactgcccgagcggc agcttagccgccaccggcgcacggcgctggacgagtaccgcagcgagatggccgggctggtcaagcgcttcggtgatgacctcag caagtgcgactttatcgccgcgcagaagctggccagccggggccgcagtgccgaggaaatcggcaaggccatggccgaggca gcccagcgctggcagagcgcaagcccggccacgaagcggattacatcgagcgcaccgtcagcaaggtcatgggtctgcccagc gtccagcttgcgcgggccgagctggcacgggcaccggcaccccgccagcgaggcatggacaggggcgggccagatttcagcat gtagtgcttgcgttggtactcacgcctgttatactatgagtactcacgcacagaaggggggtttatggaatacgaaaaaagcgcttcagg gtcggtctacctgatcaaaagtgacaagggctattggttgcccggtggctttggttatacgtcaaacaaggccgaggctggccgcttttc agtcgctgatatggccagccttaaccttgacggctgcaccttgtccttgttccgcgaagacaagcctttcggccccggcaagtttctcggt gactgatatgaaagaccaaaaggacaagcagaccggcgacctgctggccagccctgacgctgtacgccaagcgcgatatgccg agcgcatgaaggccaaagggatgcgtcagcgcaagttctggctgaccgacgacgaatacgaggcgctgcgcgagtgcctggaag aactcagagcggcgcagggcggggtagtgaccccgccagcgcctaaccaccaactgcctgcaaaggaggcaatcaatggcta
```

-continued cccataagcctatcaatattctggaggcgttcgcagcagcgccgccaccgctggactacgttttgcccaacatggtggccggtacggt cggggcgctggtgtcgcccggtggtgccggtaaatccatgctggccctgcaactggccgcacagattgcaggcgggccggatctgct ggaggtgggcgaactgcccaccggcccggtgatctacctgcccgccgaagacccgcccaccgccattcatcaccgcctgcacgcc cttggggcgcacctcagcgccgaggaacggcaagccgtggctgacggcctgctgatccagccgctgatcggcagcctgcccaaca tcatgg (nucleotide sequence of plasmid pClikCMΔfruA)

SEQ ID NO: 23 tcgagtaggagtaactcaaggtcaccgtttgcgttttgttgccgaaggtgcgcaggcacagcaggcgattgaagccatcgctaaaga aattgcggcgggcttgggtgagcctgtttccgccgttccgccggcagaaccggatactattgaagtcgctaacccggcgacaccgga agttgagcaaccaaaatccgacagtatcgaagcggttttgtgattaataatgaaaacggtctgcatgctcgtcctgcggcgactttagt gaatgaagtcaaaaaatataatgcgtcggtggcggttcgtaatttagatcgcgacggtgggttagtgagcgctaaaagcatgatgaaa atcgttgcattaggtgcgacaaaaggttctcgtctgcattttgtcgccaccggtgaagaagctcaacaagcgattgacggtatcggtgc ggcaatcgcggcaggtttaggagaataaacaatggcaaaagtggcaacaattacattaaacgccgcctatgatttggtcgggcgttta aaaacgcattgaattgggcgaagtgaatacggtggaaaccctcggtttattccctgccggtaaaggtatcaatgtggctaaggtgttgaa tgacttagatgttgaagtcgcggtcggtggttttctcggtgaagataacgtaggcgatttcgagcatttattccaacaacaaggtttgcag gataaattccagcgggttgccggtaaaacccgaataaacgtaaaaatcaccgaaacggacgcggatgtaacggatttgaattttcttg gttatcaaatcagtgaacaggattggcggaaatttaccgcagattctctcgcttattgtaaagaattcgacatcgttgccgtgtgtggcagt ttgccccgcggcgtaacggcggatatgtttcaaagctggttaagtcaattacatcaagcgggtgtaaaagtcgtactagatagtagtaat gccgcattaacagcaggtcttaaagcaaatccttggttagtgaaaccgaatcaccgcgaattagaagcctgggtcggccatgagttac cgactttgaaagacatcattgacgccgcaaaacaattaaaagcacaaggatagccaatgttattatttccatgggcgcaaacggct cattatggctaagtgataacggcgtgattttggctcagccgccgaaatgtgaaaacgtagtaagcacagtcggtgccggcgattcgat ggtcgcaggtttaatttatggttttgtaaataatttatctcaacaagaaacattggcgtttgcaagtgcggtatctgccttcgccgtttcacaa agtaacgtaggtgtcagtgatcgcaagttgctcgacccaatcttagcaaatgtaaaaatcacaacgattgaaggataagccgatgaat attttttcttacgcaatcaccaaatttaggtcgtgcaaaagcgttttattgcaccaggttttggctgccgcagtaaaacaatttcctaatcaa gcataaagcctttgttttatctcaaaacaaaggcttttttttataagtattccgctttgcccgaactaatagaaaaattggcagacaaaagaa gtgttcatagcacaggaggaacaatatggatttcaatgcaattttaaatcaagttttaagtgccgctcaggaaaccgttaagaaaacgg caagcggcaatagcacaacggataaagtggcaaaaatcggtggcggtgcagcggctatcggcgtgctttcgatgattttcgggcgc accggcggagcggggcttgcaaaattaggctcgcttgccgcattaggcagccttgcttatcaggcttaccaggattatcaacataaac aaagccaagttgtaccggttactgaaacggaatttacccaaagcgtacaacaatcggcggaactcagcaaagtgatttttgcaggca atgattgcggcggcggctgcagacggcgcgatttccgaccaggaacaacaagcgattttaagccaagccggcgatgatgcggaag tacagcagtggattcggcaagaaatgtatcaaccggcaacagtgcgggaaatcgcccaacaagtgggtgataatcaggcattagc atcacaggtgtatctggcggcaagaatggtttgcgccgatttgcacgcaaagaaattgttttcttagcaaatttagcgcaagcgttggg gttagatgaagcgcttgtagaacagttagaaaaacaggcgggtttctgatttaatcattccgcgatgtgcaaagtgcggtcaaaaataa cgatttttttaccgcacttttgcatttgcaagacgtttcgaaaatgcctgttctaacttctattaaaaccccttcttctaaaattttctccaataactc aaaataccagcaacactcgtttgggagtaatggtttgataaggacggtagaggtaaattccccaaatcaaggtttcctcattagaaag actacttgtaactcgccggaatcaagataggatttacagtcatgatacattatcggcgcgaaaatcctgccggataagaccgccggta acaagcttttaatatcgctggtgataaccgtcggcttagttagaattatgggttgttcacccatcatccagtcccatactttgccggtcttagg atttaaaatatagcctaccggaaaattggcggctaaatcaaaaacgtcttttggcaatccggttttagcgataagactaggtgctgccac gataggctcttgtaggtcagtaatcttttcgccacccaatgatcttcgggcgtgcggctgatgcgaataccgatatcaatttggtcatcca ccgctttgagcgtatcgaaatccgtgcgccagtcaatctgaatatccgatagggcgcaagtgcggttagtaatcgcaataaaattttat ccgcataatcggaaggcggtaacgtaatccgcactaagccggaaaggctctcttccgcatctagactccataggccgctttcctggctt tgcttccagatgtatgctctcctccggagagtaccgtgactttattttcggcacaaatacaggggtcgatggataaatacggcgatagttt -continued

```
cctgacggatgatccgtatgtaccggcggaagacaagctgcaaacctgtcagatggagattgatttaatggcggatgtgctgagagc
accgccccgtgaatccgcagaactgatccgctatgtgtttgcggatgattggccggaataaataaagccgggcttaatacagattaag
cccgtatagggtattattactgaataccaaacagcttacggaggacggaatgttacccattgagacaaccagactgccttctgattatta
atattttcactattaatcagaaggaataaccatgaattttacccggattgacctgaatacctggaatcgcagggaacactttgccctttat
cgtcagcagattaaatgcggattcagcctgaccaccaaactcgatattaccgctttgcgtaccgcactggcggagacaggttataagtt
ttatccgctgatgatttacctgatctcccgggctgttaatcagtttccggagttccggatggcactgaaagacaatgaacttatttactggg
accagtcagacccggtctttactgtctttcataaagaaaccgaaacattctctgcactgtcctgccgttattttccggatctcagtgagtttat
ggcaggttataatgcggtaacggcagaatatcagcatgataccagattgtttccgcagggaaatttaccggagaatcacctgaatatat
catcattaccgtgggtgagttttgacgggatttaacctgaacatcaccggaaatgatgattattttgccccg0ttacgatggcaaagttt
cagcaggaaggtgaccgcgtattattacctgtttctgtacaggttcatcatgcagtctgtgatggctttcatgcagcacggtttattaataca
cttcagctgatgtgtgataacatactgaaataaattaattaattctgtatttaagccaccgtatccggcaggaatggtggctttttttttatatttt
aaccgtaatctgtaatttcgtttcagactggtcaggatgagctcgcttggactcctgttgatagatccagtaatgacctcagaactccatct
ggatttgttcagaacgctcggttgccgccgggcgttttttattggtgagaatccaagcactagcggcgcgccggccggcccggtgtgaa
ataccgcacagatgcgtaaggagaaaataccgcatcaggcgctcttccgcttcctcgctcactgactcgctgcgctcggtcgttcggct
gcggcgagcggtatcagctcactcaaaggcggtaatacggttatccacagaatcaggggataacgcaggaaagaacatgtgagc
aaaaggccagcaaaaggccaggaaccgtaaaaaggccgcgttgctggcgtttttccataggctccgcccccctgacgagcatcac
aaaaatcgacgctcaagtcagaggtggcgaaacccgacaggactataaagataccaggcgtttccccctggaagctccctcgtgc
gctctcctgttccgaccctgccgcttaccggatacctgtccgcctttctcccttcgggaagcgtggcgctttctcatagctcacgctgtaggt
atctcagttcggtgtaggtcgttcgctccaagctgggctgtgtgcacgaaccccccgttcagcccgaccgctgcgccttatccggtaact
atcgtcttgagtccaacccggtaagacacgacttatcgccactggcagcagccactggtaacaggattagcagagcgaggtatgtag
gcggtgctacagagttcttgaagtggtggcctaactacggctacactagaaggacagtatttggtatctgcgctctgctgaagccagtta
ccttcggaaaaagagttggtagctcttgatccggcaaacaaaccaccgctggtagcggtggtttttttgtttgcaagcagcagattacgc
gcagaaaaaaaggatctcaagaagatcctttgatcttttctacggggtctgacgctcagtggaacgaaaactcacgttaagggattttg
gtcatgagattatcaaaaaggatcttcacctagatccttttaaaggccggccgcggccgccatcggcattttcttttgcgtttttatttgttaac
tgttaattgtccttgttcaaggatgctgtctttgacaacagatgttttcttgcctttgatgttcagcaggaagctcggcgcaaacgttgattgttt
gtctgcgtagaatcctctgtttgtcatatagcttgtaatcacgacattgtttcctttcgcttgaggtacagcgaagtgtgagtaagtaaaggtt
acatcgttaggatcaagatccatttttaacacaaggccagttttgttcagcggcttgatgggccagttaaagaattagaaacataacca
agcatgtaaatatcgttagacgtaatgccgtcaatcgtcattttgatccgcgggagtcagtgaacaggtaccatttgccgttcattttaaa
gacgttcgcgcgttcaatttcatctgttactgtgttagatgcaatcagcggtttcatcacttttttcagtgtgtaatcatcgtttagctcaatcata
ccgagagcgccgtttgctaactcagccgtgcgttttttatcgctttgcagaagttttgactttcttgacggaagaatgatgtgcttttgccata
gtatgctttgttaaataaagattcttcgccttggtagccatcttcagttccagtgtttgcttcaaatactaagtatttgtggcctttatcttctacgt
agtgaggatctctcagcgtatggttgtcgcctgagctgtagttgccttcatcgatgaactgctgtacattttgatacgttttccgtcaccgtca
aagattgatttataatcctctacaccgttgatgttcaaagagctgtctgatgctgatacgttaacttgtgcagttgtcagtgtttgtttgccgtaa
tgtttaccggagaaatcagtgtagaataaacggattttccgtcagatgtaaatgtggctgaacctgaccattcttgtgtttggtcttttagga
tagaatcatttgcatcgaatttgtcgctgtctttaaagacgcggccagcgttttccagctgtcaatagaagtttcgccgacttttttgataaa
catgtaaatcgatgtgtcatccgcattttaggatctccggctaatgcaaagacgatgtggtagccgtgatagtttgcgacagtgccgtca
gcgttttgtaatggccagctgtcccaaacgtccaggccttttgcagaagagatatttttaattgtggacgaatcaaattcagaaacttgata
ttttcatttttttgctgttcagggatttgcagcatatcatggcgtgtaatatgggaaatgccgtatgtttccttatatggcttttggttcgtttctttcg
caaacgcttgagttgcgcctcctgccagcagtgcggtagtaaaggttaatactgttgcttgttttgcaaacttttttgatgttcatcgttcatgtc
tccttttttatgtactgtgttagcggtctgcttcttccagccctcctgtttgaagatggcaagttagttacgcacaataaaaaaagacctaaa
```

-continued

```
atatgtaaggggtgacgccaaagtatacactttgccctttacacattttaggtcttgcctgctttatcagtaacaaacccgcgcgatttacttt tcgacctcattctattagactctcgtttggattgcaactggtctattttcctcttttgtttgatagaaaatcataaaaggatttgcagactacggg cctaaagaactaaaaaatctatctgtttcttttcattctctgtatttttatagtttctgttgcatgggcataaagttgccttttta atcacaattcag aaaatatcataatatctcatttcactaaataatagtgaacggcaggtatatgtgatgggttaaaaaggatcggcggccgctcgatttaaa tc
```

---

The invention claimed is:

1. A process of producing an organic compound, the process comprising:
   I) cultivating a genetically modified microorganism in a culture medium comprising sucrose as an assimilable carbon source to allow the genetically modified microorganism to produce the organic compound, and
   II) recovering the organic compound from the fermentation broth obtained in process step I),
   wherein the genetically modified microorganism comprises:
   C) at least one genetic modification that leads to an increased activity of the enzyme encoded by the rbsK-gene, compared to the original microorganism that has not been genetically modified,
   and wherein the original microorganism belongs to the family Pasteurellaceae.

2. The process according to claim 1, wherein the organic compound is succinic acid.

3. The process according to claim 1, wherein the original microorganism belongs to the genus Basfia.

4. The process according to claim 3, wherein the original microorganism belongs to the species *Basfia succiniciproducens*.

5. The process according to claim 4, wherein the original microorganism is *Basfia succiniciproducens* strain DD1 as deposited under DSM 18541 with the DSMZ, Germany.

6. The process according to claim 1, wherein the rbsK-gene comprises a nucleic acid selected from the group consisting of:
   a1) nucleic acids having the nucleotide sequence of SEQ ID NO: 3;
   b1) nucleic acids encoding the amino acid sequence of SEQ ID NO: 4;
   c1) nucleic acids which are at least 70% identical to the nucleic acid of a1) or b1), the identity being the identity over the total length of the nucleic acids of a1) or b1);
   d1) nucleic acids encoding an amino acid sequence which is at least 70% identical to the amino acid sequence encoded by the nucleic acid of a1) or b1), the identity being the identity over the total length of amino acid sequence encoded by the nucleic acids of a1) or b1);
   e1) nucleic acids capable of hybridizing under stringent conditions with a complementary sequence of any of the nucleic acids according to a1) or b1), wherein the stringent conditions are conditions wherein 100 contiguous nucleotides or more, which are a fragment or identical to the complementary sequence of any of the nucleic acids according to a1) or b1), hybridize under conditions equivalent to hybridization in 7% SDS, 0.5 M NaPO4, 1 mM EDTA at 50° C., with washing in 2×SSC, 0.1% SDS at 50° C.; and
   f1) nucleic acids encoding the same protein as any of the nucleic acids of a1) or b1), but differing from the nucleic acids of a1) or b1) above due to the degeneracy of the genetic code.

7. The process according to claim 1, wherein the at least one genetic modification C) comprises a modification of the rbsK-gene, a modification of a regulatory element of the rbsK-gene, or a combination of both.

8. The process according to claim 7, wherein the at least one genetic modification C) comprises an overexpression modification of the rbsK-gene.

9. The process according to claim 1, wherein the genetically modified microorganism additionally comprises:
   D) at least one genetic modification that leads to a reduced activity of the enzyme encoded by the fruA-gene, compared to the original microorganism that has not been genetically modified.

10. The process according to claim 9, wherein the fruA-gene comprises a nucleic acid selected from the group consisting of:
    a2) nucleic acids having the nucleotide sequence of SEQ ID NO: 5;
    b2) nucleic acids encoding the amino acid sequence of SEQ ID NO: 6;
    c2) nucleic acids which are at least 70% identical to the nucleic acid of a2) or b2), the identity being the identity over the total length of the nucleic acids of a2) or b2);
    d2) nucleic acids encoding an amino acid sequence which is at least 70% identical to the amino acid sequence encoded by the nucleic acid of a2) or b2), the identity being the identity over the total length of amino acid sequence encoded by the nucleic acids of a2) or b2);
    e2) nucleic acids capable of hybridizing under stringent conditions with a complementary sequence of any of the nucleic acids according to a2) or b2), wherein the stringent conditions are conditions wherein 100 contiguous nucleotides or more, which are a fragment or identical to the complementary sequence of any of the nucleic acids according to a2) or b2), hybridize under conditions equivalent to hybridization in 7% SDS, 0.5 M NaPO4, 1 mM EDTA at 50° C., with washing in 2×SSC, 0.1% SDS at 50° C.; and
    f2) nucleic acids encoding the same protein as any of the nucleic acids of a2) or b2), but differing from the nucleic acids of a2) or b2) above due to the degeneracy of the genetic code.

11. The process according to claim 10, wherein the at least one genetic modification D) comprises a modification of the fruA-gene, a modification of a regulatory element of the fruA-gene, or a combination of both.

12. The process according to claim 11, wherein the at least one modification D) comprises an inactivation of the fruA-gene.

13. A genetically modified microorganism that comprises:
   A) at least one genetic modification that leads to an increased activity of the enzyme encoded by the rbsK-gene, compared to the original microorganism that has not been genetically modified,
   wherein the original microorganism belongs to the family Pasteurellaceae.

14. The genetically modified microorganism according to claim 13, wherein the at least one genetic modification A) comprises a modification of the rbsK-gene, a modification of a regulatory element of the rbsK-gene, or a combination of both.

15. The genetically modified microorganism according to claim 14, wherein the at least one genetic modification A) comprises an overexpression modification of the rbsK-gene.

16. The genetically modified microorganism according to claim 13, further comprising:
   B) at least one genetic modification that leads to a reduced activity of the enzyme encoded by the fruA-gene, compared to the original microorganism that has not been genetically modified.

17. The genetically modified microorganism according to claim 16, wherein the fruA-gene comprises a nucleic acid selected from the group consisting of:
   a2) nucleic acids having the nucleotide sequence of SEQ ID NO: 5;
   b2) nucleic acids encoding the amino acid sequence of SEQ ID NO: 6;
   c2) nucleic acids which are at least 70% identical to the nucleic acid of a2) or b2), the identity being the identity over the total length of the nucleic acids of a2) or b2);
   d2) nucleic acids encoding an amino acid sequence which is at least 70% identical to the amino acid sequence encoded by the nucleic acid of a2) or b2), the identity being the identity over the total length of amino acid sequence encoded by the nucleic acids of a2) or b2);
   e2) nucleic acids capable of hybridizing under stringent conditions with a complementary sequence of any of the nucleic acids according to a2) or b2), wherein the stringent conditions are conditions wherein 100 contiguous nucleotides or more, which are a fragment or identical to the complementary sequence of any of the nucleic acids according to a2) or b2), hybridize under conditions equivalent to hybridization in 7% SDS, 0.5 M NaPO4, 1 mM EDTA at 50° C., with washing in 2×SSC, 0.1% SDS at 50° C.; and
   f2) nucleic acids encoding the same protein as any of the nucleic acids of a2) or b2), but differing from the nucleic acids of a2) or b2) above due to the degeneracy of the genetic code.

18. The genetically modified microorganism according to claim 17, wherein the at least one genetic modification B) comprises a modification of the fruA-gene, a modification of a regulatory element of the fruA-gene, or a combination of both.

19. The genetically modified microorganism according to claim 18, wherein the at least one modification B) comprises an inactivation of the fruA-gene.

\* \* \* \* \*

SEQUENCE LISTING

<160> NUMBER OF SEQ ID NOS: 23

<210> SEQ ID NO 1
<211> LENGTH: 1517
<212> TYPE: DNA
<213> ORGANISM: Basfia succiniciproducens
<220> FEATURE:
<221> NAME/KEY: MISC_FEATURE
<223> OTHER INFORMATION: 16 S rDNA of strain DD1

<400> SEQUENCE: 1

```
tttgatcctg gctcagattg aacgctggcg gcaggcttaa cacatgcaag tcgaacggta      60
gcgggaggaa agcttgcttt ctttgccgac gagtggcgga cgggtgagta atgcttgggg     120
atctggctta tggaggggga taacgacggg aaactgtcgc taataccgcg taatatcttc     180
ggattaaagg gtgggacttt cgggccaccc gccataagat gagcccaagt gggattaggt     240
agttggtggg gtaaaggcct accaagccga cgatctctag ctggtctgag aggatgacca     300
gccacactgg aactgagaca cggtccagac tcctacggga ggcagcagtg gggaatattg     360
cacaatgggg gaaccctga tgcagccatg ccgcgtgaat gaagaaggcc ttcgggttgt      420
aaagttcttt cggtgacgag gaaggtgttt gtttttaatag gacaagcaat tgacgttaat    480
cacagaagaa gcaccggcta actccgtgcc agcagccgcg gtaatacgga gggtgcgagc    540
gttaatcgga ataactgggc gtaaagggca tgcaggcgga cttttaagtg agatgtgaaa    600 gcccccgggct taacctggga attgcatttc agactgggag tctagagtac tttagggagg    660
ggtagaattc cacgtgtagc ggtgaaatgc gtagagatgt ggaggaatac cgaaggcgaa    720
ggcagcccct tgggaagata ctgacgctca tatgcgaaag cgtggggagc aaacaggatt    780
agataccctg gtagtccacg cggtaaacgc tgtcgatttg gggattgggc tttaggcctg    840
gtgctcgtag ctaacgtgat aaatcgaccg cctgggagt acggccgcaa ggttaaaact    900
caaatgaatt gacggggggcc cgcacaagcg gtggagcatg tggtttaatt cgatgcaacg    960
cgaagaacct tacctactct tgacatccag agaatcctgt agagatacgg gagtgccttc   1020
gggagctctg agacaggtgc tgcatggctg tcgtcagctc gtgttgtgaa atgttgggtt   1080
aagtcccgca acgagcgcaa cccttatcct ttgttgccag catgtaaaga tgggaactca   1140
aaggagactg ccggtgacaa accggaggaa ggtggggatg acgtcaagtc atcatggccc   1200
ttacgagtag ggctacacac gtgctacaat ggtgcataca gagggcggcg ataccgcgag   1260
gtagagcgaa tctcagaaag tgcatcgtag tccggattgg agtctgcaac tcgactccat   1320
gaagtcggaa tcgctagtaa tcgcaaatca gaatgttgcg gtgaatacgt tcccgggcct   1380
tgtacacacc gcccgtcaca ccatgggagt gggttgtacc agaagtagat agcttaacct   1440
tcgggggggg cgtttaccac ggtatgattc atgactgggg tgaagtcgta acaaggtaac   1500 cgtagggga acctgcgg                                                  1517
```

```
<210> SEQ ID NO 2
<211> LENGTH: 3008
<212> TYPE: DNA
<213> ORGANISM: Basfia succiniciproducens
<220> FEATURE:
<221> NAME/KEY: MISC_FEATURE
<223> OTHER INFORMATION: 23 S rDNA of strain DD1

<400> SEQUENCE: 2
agtaataacg aacgacacag gtataagaat acttgaggtt gtatggttaa gtgactaagc      60
gtacaaggtg gatgccttgg caatcagagg cgaagaagga cgtgctaatc tgcgaaaagc     120
ttgggtgagt tgataagaag cgtctaaccc aagatatccg aatggggcaa cccagtagat     180
gaagaatcta ctatcaataa ccgaatccat aggttattga ggcaaaccgg agaactgaa      240 acatctaagt accccgagga aaagaaatca accgagatta cgtcagtagc ggcgagcgaa     300
agcgtaagag ccggcaagtg atagcatgag gattagagga atcggctggg aagccgggcg     360
gcacagggtg atagccccgt acttgaaaat cattgtgtgg tactgagctt gcgagaagta     420
gggcgggaca cgagaaaatcc tgtttgaaga agggggggacc atcctccaag gctaaatact     480
cctgattgac cgatagtgaa ccagtactgt gaaggaaagg cgaaaagaac cccggtgagg     540
ggagtgaaat agaacctgaa accttgtacg tacaagcagt gggagcccgc gagggtgact     600
gcgtaccttt tgtataatgg gtcagcgact tatattatgt agcgaggtta accgaatagg     660
ggagccgaag ggaaaccgag tcttaactgg gcgtcgagtt gcatgatata gacccgaaac     720
ccggtgatct agccatgggc aggttgaagg ttgggtaaca ctaactggag gaccgaaccg     780
actaatgttg aaaaattagc ggatgacctg tggctggggg tgaaaggcca atcaaaccgg     840
gagatagctg gttctccccg aaatctattt aggtagagcc ttatgtgaat accttcgggg     900
gtagagcact gtttcggcta gggggccatc ccggcttacc aacccgatgc aaactgcgaa     960
taccgaagag taatgcatag gagacacacg gcgggtgcta acgttcgtcg tggagaggga    1020
aacaacccag accgccagct aaggtcccaa agtttatatt aagtgggaaa cgaagtggga    1080
aggcttagac agctaggatg ttggcttaga agcagccatc atttaaagaa agcgtaatag    1140
ctcactagtc gagtcggcct gcgcggaaga tgtaacgggg ctcaaatata gcaccgaagc    1200
tgcggcatca ggcgtaagcc tgttgggtag gggagcgtcg tgtaagcgga agaaggtggt    1260
tcgagagggc tgctggacgt atcacgagtg cgaatgctga cataagtaac gataaaacgg    1320
gtgaaaaacc cgttcgccgg aagaccaagg gttcctgtcc aacgttaatc ggggcagggt    1380
gagtcggccc ctaaggcgag gctgaagagc gtagtcgatg ggaaacgggt taatattccc    1440
gtacttgtta taattgcgat gtggggacgg agtaggttag gttatcgacc tgttggaaaa    1500
ggtcgtttaa gttggtaggt ggagcgttta ggcaaatccg gacgcttatc aacaccgaga    1560
gatgatgacg aggcgctaag gtgccgaagt aaccgatacc acacttccag gaaaagccac    1620
taagcgtcag attataataa accgtactat aaaccgacac aggtggtcag gtagagaata    1680
ctcaggcgct tgagagaact cggggtgaagg aactaggcaa aatagcaccg taacttcggg    1740
agaaggtgcg ccggcgtaga ttgtagaggt atacccttga aggttgaacc ggtcgaagtg    1800
acccgctggc tgcaactgtt tattaaaaac acagcactct gcaaacacga aagtggacgt    1860
atagggtgtg atgcctgccc ggtgctggaa ggttaattga tggcgttatc gcaagagaag    1920
cgcctgatcg aagccccagt aaacggcggc cgtaactata acggtcctaa ggtagcgaaa    1980
ttccttgtcg ggtaagttcc gacctgcacg aatggcataa tgatggccag gctgtctcca    2040
cccgagactc agtgaaattg aaatcgccgt gaagatgcgg tgtacccgcg gctagacgga    2100
```

```
aagaccccgt gaacctttac tatagcttga cactgaacct tgaattttga tgtgtaggat   2160
aggtgggagg ctttgaagcg gtaacgccag ttatcgtgga gccatccttg aaataccacc   2220 cttttaacgtt tgatgttcta acgaagtgcc cggaacgggt actcggacag tgtctggtgg   2280
gtagtttgac tggggcggtc tcctcccaaa gagtaacgga ggagcacgaa ggtttgctaa   2340
tgacggtcgg acatcgtcag gttagtgcaa tggtataagc aagcttaact gcgagacgga   2400
caagtcgagc aggtgcgaaa gcaggtcata gtgatccggt ggttctgaat ggaagggcca   2460
tcgctcaacg gataaaaggt actccgggga taacaggctg ataccgccca gagttcata   2520 tcgacggcgg tgtttggcac ctcgatgtcg gctcatcaca tcctggggct gaagtaggtc   2580
ccaagggtat ggctgttcgc catttaaagt ggtacgcgag ctgggtttaa acgtcgtga   2640 gacagtttgg tccctatctg ccgtgggcgt tggagaattg agaggggctg ctcctagtac   2700
gagaggaccg gagtggacgc atcactggtg ttccggttgt gtcgccagac gcattgccgg   2760
gtagctacat gcggaagaga taagtgctga aagcatctaa gcacgaaact tgcctcgaga   2820
tgagttctcc cagtatttaa tactgtaagg gttgttggag acgacgacgt agataggccg   2880
ggtgtgtaag cgttgcgaga cgttgagcta accggtacta attgcccgag aggcttagcc   2940
atacaacgct caagtgtttt tggtagtgaa agttattacg gaataagtaa gtagtcaggg   3000
aatcggct                                                           3008

<210> SEQ ID NO 3
<211> LENGTH: 933
<212> TYPE: DNA
<213> ORGANISM: Basfia succiniciproducens
<220> FEATURE:
<221> NAME/KEY: MISC_FEATURE
<223> OTHER INFORMATION: nucleotide sequence of rbsK-gene from strain
      DD1

<400> SEQUENCE: 3
atgcatatga caaacaaaat ttgggtatta ggcgatgccg tggtggattt aattcctgac     60
ggagacaacc attatttgcg ttgcgcaggc ggcgcaccgg ctaatgtggc ggtcggcgtt    120
gcccgtttag gtgtgcctag cgcatttatc ggccgtgtag gtaaagatcc gttagggaa    180 tttatgcgcg atacgctgaa tcaggaaaat gtaaacaccg attatatgtt gttagatcct    240
aaacaacgta cttcgacggt ggtggttgga ttaaccgacg gcgaacgtag ttttaccttt    300
atggtgaatc caagtgcgga tcaatttta caaatttccg atctgccgca atttcaagcc    360
ggagactggt tgcactgctg ctctatcgcc ttaatcaatg aaccgacccg cagcgctact    420
ttcacggcaa tgaaaaatat ccgtgcggcc ggcggtaaag tatctttcga tccgaattta    480
cgcgaaagct tatggaaatc ccaggatgaa atgatcgatg tggtgatgga agcggtaagc    540
cttgccgacg tattgaaatt ttcagaagaa gaattaacgc tgttaaccca taccgacagc    600
ctggaaaaat cttttgaaaa aatcaccgca ctttatcccg ataaattgat tatttgtcact    660 ttagggaaag atggcgcgct ctatcatctg cacggtaaaa aagaggtggt tgcagggaaa    720
gcgctgaaac cggtagatac caccggtgcc ggcgacgctt ttgtcagcgg gttattagcc    780
ggattatcac aaacggaaaa ctggcagcaa cctgaacaac tcgttactat tattcgccag    840
gccaacgcca gcggcgcgct tgccacaacg gcaaaaggcg ctatgtcggc attaccgaat    900
cggcaacaat tagcggaatt tttagcaaac taa                                 933

<210> SEQ ID NO 4
```

<211> LENGTH: 310
<212> TYPE: PRT
<213> ORGANISM: Basfia succiniciproducens
<220> FEATURE:
<221> NAME/KEY: SITE
<222> LOCATION: (1)..(310)
<223> OTHER INFORMATION: amino acid sequence of RbsK from strain DD1

<400> SEQUENCE: 4

```
Met His Met Thr Asn Lys Ile Trp Val Leu Gly Asp Ala Val Asp
1               5                   10                  15

Leu Ile Pro Asp Gly Asp Asn His Tyr Leu Arg Cys Ala Gly Ala
                20                  25                  30

Pro Ala Asn Val Ala Val Gly Val Ala Arg Leu Gly Val Pro Ser Ala
                35                  40                  45

Phe Ile Gly Arg Val Gly Lys Asp Pro Leu Gly Glu Phe Met Arg Asp
    50                  55                  60

Thr Leu Asn Gln Glu Asn Val Asn Thr Asp Tyr Met Leu Leu Asp Pro
65                  70                  75                  80

Lys Gln Arg Thr Ser Thr Val Val Val Gly Leu Thr Asp Gly Glu Arg
                85                  90                  95

Ser Phe Thr Phe Met Val Asn Pro Ser Ala Asp Gln Phe Leu Gln Ile
                100                 105                 110

Ser Asp Leu Pro Gln Phe Gln Ala Gly Asp Trp Leu His Cys Cys Ser
                115                 120                 125

Ile Ala Leu Ile Asn Glu Pro Thr Arg Ser Ala Thr Phe Thr Ala Met
    130                 135                 140

Lys Asn Ile Arg Ala Ala Gly Gly Lys Val Ser Phe Asp Pro Asn Leu
145                 150                 155                 160

Arg Glu Ser Leu Trp Lys Ser Gln Asp Glu Met Ile Asp Val Val Met
                165                 170                 175

Glu Ala Val Ser Leu Ala Asp Val Leu Lys Phe Ser Glu Glu Glu Leu
                180                 185                 190

Thr Leu Leu Thr His Thr Asp Ser Leu Glu Lys Ser Phe Glu Lys Ile
                195                 200                 205

Thr Ala Leu Tyr Pro Asp Lys Leu Ile Ile Val Thr Leu Gly Lys Asp
    210                 215                 220

Gly Ala Leu Tyr His Leu His Gly Lys Lys Glu Val Val Ala Gly Lys
225                 230                 235                 240

Ala Leu Lys Pro Val Asp Thr Gly Ala Gly Asp Ala Phe Val Ser
                245                 250                 255

Gly Leu Leu Ala Gly Leu Ser Gln Thr Glu Asn Trp Gln Gln Pro Glu
                260                 265                 270

Gln Leu Val Thr Ile Ile Arg Gln Ala Asn Ala Ser Gly Ala Leu Ala
                275                 280                 285

Thr Thr Ala Lys Gly Ala Met Ser Ala Leu Pro Asn Arg Gln Gln Leu
    290                 295                 300

Ala Glu Phe Leu Ala Asn
305                 310
```

<210> SEQ ID NO 5
<211> LENGTH: 1695
<212> TYPE: DNA
<213> ORGANISM: Basfia succiniciproducens
<220> FEATURE:
<221> NAME/KEY: MISC_FEATURE
<223> OTHER INFORMATION: nucleotide sequence of fruA-gene from strain DD1

<400> SEQUENCE: 5

```
ttgaaggata agccgatgaa tatttttctt acgcaatcac caaatttagg tcgtgcaaaa      60
gcgtttttat tgcaccaggt tttggctgcc gcagtaaaac aacaaaatca tcaactggta     120
gaaaatgccg aacaagcgga tttagcgatt gttttcggta aactttgcc gaatttgacc      180
gcacttttag gtaaaaaagt gtatttggcg gatgaagaac aagcgttgaa tgcgcctgaa     240
aataccgtcg cgcaggcatt aaccgaggct gtggattatg ttcaaccggc aacaggac      300
gtgcaacccg caactgcttc cggtatgaaa aatatcgtgg cggttaccgc ttgtccgacc     360
ggggtggcgc acaccttttat gtctgccgag gcgattacaa cctactgcca acagcaaggt    420
tggaatgtaa aagtggaaac cagaggtcaa gtcggtgcga caatattat ttctgcggaa      480
gatgtggcgg cggccgattt agtctttatc gctacggata ttaatgtgga tttaagcaaa    540
ttcaaaggaa aaccgatgta tcgtacttca acgggcttag cattgaagaa aaccgcacag    600
gaatttgata aagcctttaa agaagcgacg atttatcagg gtgaagaaac tacaaccacc    660
acagaaacac aaacttcagg cgagaaaaaa ggtgtatata aacatcttat gaccggggtt    720
tcccatatgt taccgcttgt cgttgccggc ggttattga ttgctatttc gtttatgttc     780
ggtattgagg cgtttaaaga cgaaaacatc gcaggcggct tgccgaaagc attaatggat    840
atcggcggcg gtgcggcgtt ccacttaatg attgccgtat ttgcaggtta tgttgcattc    900
tctattgcag accgtccggg gttagccgta ggtcttatcg gcggtatgct tgccacatcc    960
gccggtgccg gtattttggg cggtattatc gcgggttttc ttgccggtta tgtagtgaaa   1020
ttcctgaatg atgccattca actgccagcc agtttaactt cgttaaaacc gatttaatt    1080
ctgccttat taggttcggc gatcgtcggc ttggccatga tttatttatt aaatccaccg    1140
gttgctgcgg caatgaatgc gctaaccgaa tggttaaaag gtttgggctc ggcaaacgcg   1200
ctggtgttgg gtgcgattct tggcggtatg atgtgtatcg atatgggcgg tccggtaaac   1260
aaagccgctt atgtattcgg tacgggcatg attggttcac aggtttatac gccgatggct   1320
gcggtaatgg ctgcgggtat ggtaccgcct ttaggaatgg cgattgccac ctggattgcg   1380
cgcgctaaat ttaacgcaag ccaacgtgat gcgggtaaag cttcattcgt actaggttta   1440
tgctttattt ccgaaggtgc gttaccgttt gttgccgccg accctgtacg cgtgattgtt   1500
tcaagtgtaa ttggcggagc cattgccggc gcaatttcta tgagccttgc cattacgctg   1560
caagcgcctc acggcggttt attcgtgatt ccgtttgtgt cgcaaccgtt aatgtatttg    1620
ggtgcgattg ccgtaggcgc cttaacaacc ggcgttcttt acgcaattat caaaccgaaa   1680
caagctgcgg aataa                                                    1695
```

<210> SEQ ID NO 6
<211> LENGTH: 564
<212> TYPE: PRT
<213> ORGANISM: Basfia succiniciproducens
<220> FEATURE:
<221> NAME/KEY: SITE
<222> LOCATION: (1)..(564)
<223> OTHER INFORMATION: amino acid sequence of FruA from strain DD1

<400> SEQUENCE: 6

```
Met Lys Asp Lys Pro Met Asn Ile Phe Leu Thr Gln Ser Pro Asn Leu
 1               5                  10                  15

Gly Arg Ala Lys Ala Phe Leu Leu His Gln Val Leu Ala Ala Ala Val
            20                  25                  30
```

```
Lys Gln Gln Asn His Gln Leu Val Glu Asn Ala Glu Gln Ala Asp Leu
             35                  40                  45
Ala Ile Val Phe Gly Lys Thr Leu Pro Asn Leu Thr Ala Leu Leu Gly
 50                  55                  60
Lys Lys Val Tyr Leu Ala Asp Glu Gln Ala Leu Asn Ala Pro Glu
 65                  70                  75                  80
Asn Thr Val Ala Gln Ala Leu Thr Glu Ala Val Asp Tyr Val Gln Pro
                 85                  90                  95
Ala Gln Gln Asp Val Gln Pro Ala Thr Ala Ser Gly Met Lys Asn Ile
                100                 105                 110
Val Ala Val Thr Ala Cys Pro Thr Gly Val Ala His Thr Phe Met Ser
                115                 120                 125
Ala Glu Ala Ile Thr Thr Tyr Cys Gln Gln Gln Gly Trp Asn Val Lys
    130                 135                 140
Val Glu Thr Arg Gly Gln Val Gly Ala Asn Asn Ile Ile Ser Ala Glu
145                 150                 155                 160
Asp Val Ala Ala Ala Asp Leu Val Phe Ile Ala Thr Asp Ile Asn Val
                165                 170                 175
Asp Leu Ser Lys Phe Lys Gly Lys Pro Met Tyr Arg Thr Ser Thr Gly
                180                 185                 190
Leu Ala Leu Lys Lys Thr Ala Gln Glu Phe Asp Lys Ala Phe Lys Glu
            195                 200                 205
Ala Thr Ile Tyr Gln Gly Glu Thr Thr Thr Thr Glu Thr Gln
    210                 215                 220
Thr Ser Gly Glu Lys Lys Gly Val Tyr Lys His Leu Met Thr Gly Val
225                 230                 235                 240
Ser His Met Leu Pro Leu Val Val Ala Gly Gly Leu Leu Ile Ala Ile
                245                 250                 255
Ser Phe Met Phe Gly Ile Glu Ala Phe Lys Asp Glu Asn Ile Ala Gly
                260                 265                 270
Gly Leu Pro Lys Ala Leu Met Asp Ile Gly Gly Ala Ala Phe His
            275                 280                 285
Leu Met Ile Ala Val Phe Ala Gly Tyr Val Ala Phe Ser Ile Ala Asp
    290                 295                 300
Arg Pro Gly Leu Ala Val Gly Leu Ile Gly Gly Met Leu Ala Thr Ser
305                 310                 315                 320
Ala Gly Ala Gly Ile Leu Gly Gly Ile Ile Ala Gly Phe Leu Ala Gly
                325                 330                 335
Tyr Val Val Lys Phe Leu Asn Asp Ala Ile Gln Leu Pro Ala Ser Leu
                340                 345                 350
Thr Ser Leu Lys Pro Ile Leu Ile Leu Pro Leu Leu Gly Ser Ala Ile
            355                 360                 365
Val Gly Leu Ala Met Ile Tyr Leu Leu Asn Pro Val Ala Ala Ala
    370                 375                 380
Met Asn Ala Leu Thr Glu Trp Leu Lys Gly Leu Gly Ser Ala Asn Ala
385                 390                 395                 400
Leu Val Leu Gly Ala Ile Leu Gly Gly Met Met Cys Ile Asp Met Gly
                405                 410                 415
Gly Pro Val Asn Lys Ala Ala Tyr Val Phe Gly Thr Gly Met Ile Gly
                420                 425                 430
Ser Gln Val Tyr Thr Pro Met Ala Ala Val Met Ala Ala Gly Met Val
            435                 440                 445
Pro Pro Leu Gly Met Ala Ile Ala Thr Trp Ile Ala Arg Ala Lys Phe
```

```
                450             455             460
Asn Ala Ser Gln Arg Asp Ala Gly Lys Ala Ser Phe Val Leu Gly Leu
465                 470                 475                 480

Cys Phe Ile Ser Glu Gly Ala Leu Pro Phe Val Ala Ala Asp Pro Val
                485                 490                 495

Arg Val Ile Val Ser Ser Val Ile Gly Gly Ala Ile Ala Gly Ala Ile
                500                 505                 510

Ser Met Ser Leu Ala Ile Thr Leu Gln Ala Pro His Gly Gly Leu Phe
            515                 520                 525

Val Ile Pro Phe Val Ser Gln Pro Leu Met Tyr Leu Gly Ala Ile Ala
            530                 535                 540

Val Gly Ala Leu Thr Thr Gly Val Leu Tyr Ala Ile Ile Lys Pro Lys
545                 550                 555                 560

Gln Ala Ala Glu

<210> SEQ ID NO 7
<211> LENGTH: 315
<212> TYPE: DNA
<213> ORGANISM: Basfia succiniciproducens
<220> FEATURE:
<221> NAME/KEY: MISC_FEATURE
<223> OTHER INFORMATION: nucleotide sequence of ackA-promoter from
      strain DD1

<400> SEQUENCE: 7 ccgaatatttt ctgccccgcc gatatagttt taaaaaatcc cattttttaaa tccttaattt     60 atatttcttc aaattttttac tactgactta tttttaaattt gctgccatttt tatcctgttt    120 taaagatcgc ttatcgcatg aaactcaaat ggcttattgg atatatgtcc taaaaattga    180
acatttttat aacatttttgc taaaaattca attttttttg acttaaatcg cttttttcag    240
aacttcataa tttattttat tccgttaaac gtgtatcctt attatcggta acattcccaa    300
acgtctattc gttca                                                      315

<210> SEQ ID NO 8
<211> LENGTH: 1029
<212> TYPE: DNA
<213> ORGANISM: Basfia succinicproducens
<220> FEATURE:
<221> NAME/KEY: MISC_FEATURE
<223> OTHER INFORMATION: nucleotide sequence of ldhA-gene from strain
      DD1

<400> SEQUENCE: 8
ttgacaaaat cagtatgttt aaataaggag ctaactatga aagttgccgt ttacagtact     60
aaaaattatg atcgcaaaca tctggatttg gcgaataaaa aatttaattt tgagcttcat    120
ttctttgatt ttttacttga tgaacaaacc gcgaaaatgg cggagggcgc cgatgccgtc    180
tgtattttcg tcaatgatga tgcgagccgc ccggtgttaa caagttggc gcaaatcgga    240 gtgaaaatta tcgctttacg ttgtgccggt tttaataatg tggatttgga ggcggcaaaa    300
gagctgggat taaaagtcgt acgggtgcct gcgtattcgc cggaagccgt tgccgagcat    360
gcgatcggat taatgctgac tttaaaccgc cgtatccata aggcttatca gcgtacccgc    420
gatgcgaatt tttctctgga aggattggtc ggttttaata tgttcggcaa aaccgccgga    480
gtgattggta cgggaaaaat cggcttggcg gctattcgca ttttaaaagg cttcggtatg    540
gacgttctgg cgtttgatcc ttttaaaaat ccggcggcgg aagcgttggg cgcaaaatat    600
gtcggtttag acgagcttta tgcaaaatcc catgttatca ctttgcattg cccggctacg    660
```

```
gcggataatt atcatttatt aaatgaagcg gcttttaata aaatgcgcga cggtgtaatg    720
attattaata ccagccgcgg cgttttaatt gacagccggg cggcaatcga agcgttaaaa    780
cggcagaaaa tcggcgctct cggtatggat gtttatgaaa atgaacggga tttgtttttc    840
gaggataaat ctaacgatgt tattacggat gatgtattcc gtcgcctttc ttcctgtcat    900
aatgtgcttt ttaccggtca tcaggcgttt ttaacggaag aagcgctgaa taatatcgcc    960
gatgtgactt tatcgaatat tcaggcggtt tccaaaaatg caacgtgcga aaatagcgtt   1020
gaaggctaa                                                           1029
```

<210> SEQ ID NO 9
<211> LENGTH: 342
<212> TYPE: PRT
<213> ORGANISM: Basfia succiniciproducens
<220> FEATURE:
<221> NAME/KEY: SITE
<222> LOCATION: (1)..(342)
<223> OTHER INFORMATION: amino acid sequence of LdhA from strain DD1

<400> SEQUENCE: 9

```
Met Thr Lys Ser Val Cys Leu Asn Lys Glu Leu Thr Met Lys Val Ala
1               5                   10                  15

Val Tyr Ser Thr Lys Asn Tyr Asp Arg Lys His Leu Asp Leu Ala Asn
                20                  25                  30

Lys Lys Phe Asn Phe Glu Leu His Phe Phe Asp Phe Leu Asp Glu
        35                  40                  45

Gln Thr Ala Lys Met Ala Glu Gly Ala Asp Ala Val Cys Ile Phe Val
    50                  55                  60

Asn Asp Asp Ala Ser Arg Pro Val Leu Thr Lys Leu Ala Gln Ile Gly
65                  70                  75                  80

Val Lys Ile Ile Ala Leu Arg Cys Ala Gly Phe Asn Asn Val Asp Leu
                85                  90                  95

Glu Ala Ala Lys Glu Leu Gly Leu Lys Val Val Arg Val Pro Ala Tyr
            100                 105                 110

Ser Pro Glu Ala Val Ala Glu His Ala Ile Gly Leu Met Leu Thr Leu
        115                 120                 125

Asn Arg Arg Ile His Lys Ala Tyr Gln Arg Thr Arg Asp Ala Asn Phe
    130                 135                 140

Ser Leu Glu Gly Leu Val Gly Phe Asn Met Phe Gly Lys Thr Ala Gly
145                 150                 155                 160

Val Ile Gly Thr Gly Lys Ile Gly Leu Ala Ala Ile Arg Ile Leu Lys
                165                 170                 175

Gly Phe Gly Met Asp Val Leu Ala Phe Asp Pro Phe Lys Asn Pro Ala
            180                 185                 190

Ala Glu Ala Leu Gly Ala Lys Tyr Val Gly Leu Asp Glu Leu Tyr Ala
        195                 200                 205

Lys Ser His Val Ile Thr Leu His Cys Pro Ala Thr Ala Asp Asn Tyr
    210                 215                 220

His Leu Leu Asn Glu Ala Ala Phe Asn Lys Met Arg Asp Gly Val Met
225                 230                 235                 240

Ile Ile Asn Thr Ser Arg Gly Val Leu Ile Asp Ser Arg Ala Ala Ile
                245                 250                 255

Glu Ala Leu Lys Arg Gln Lys Ile Gly Ala Leu Gly Met Asp Val Tyr
            260                 265                 270

Glu Asn Glu Arg Asp Leu Phe Phe Glu Asp Lys Ser Asn Asp Val Ile
```

```
               275                 280                 285
Thr Asp Asp Val Phe Arg Arg Leu Ser Ser Cys His Asn Val Leu Phe
        290                 295                 300

Thr Gly His Gln Ala Phe Leu Thr Glu Glu Ala Leu Asn Asn Ile Ala
305                 310                 315                 320

Asp Val Thr Leu Ser Asn Ile Gln Ala Val Ser Lys Asn Ala Thr Cys
                325                 330                 335

Glu Asn Ser Val Glu Gly
            340

<210> SEQ ID NO 10
<211> LENGTH: 741
<212> TYPE: DNA
<213> ORGANISM: Basfia succiniciproducens
<220> FEATURE:
<221> NAME/KEY: MISC_FEATURE
<223> OTHER INFORMATION: nucleotide sequence of pflA-gene from strain
      DD1

<400> SEQUENCE: 10
atgtcggttt taggacgaat tcattcattt gaaacctgcg ggacagttga cgggccggga      60
atccgcttta ttttattttt acaaggctgc ttaatgcgtt gtaaatactg ccataataga     120
gacacctggg atttgcacgg cggtaaagaa atttccgttg aagaattaat gaaagaagtg     180
gtgacctatc gccatttat gaacgcctcg ggcggcggag ttaccgcttc cggcggtgaa      240 gctatttttac aggcggaatt tgtacgggac tggttcagag cctgccataa agaaggaatt     300
aatacttgct tggataccaa cggtttcgtc cgtcatcatg atcatattat tgatgaattg     360
attgatgaca cggatcttgt gttgcttgac ctgaaagaaa tgaatgaacg ggttcacgaa     420
agcctgattg gcgtgccgaa taaaagagtg ctcgaattcg caaatatttt agcggatcga     480
aatcagcgta cctggatccg ccatgttgta gtgccgggtt atacagatag tgacgaagat     540
ttgcacatgc tggggaattt cattaaagat atgaagaata tcgaaaaagt ggaattatta     600
ccttatcacc gtctaggcgc ccataaatgg gaagtactcg gcgataaata cgagcttgaa     660
gatgtaaaac cgccgacaaa agaattaatg gagcatgtta aggggttgct tgcaggctac     720
gggcttaatg tgacatatta g                                              741

<210> SEQ ID NO 11
<211> LENGTH: 246
<212> TYPE: PRT
<213> ORGANISM: Basfia succiniciproducens
<220> FEATURE:
<221> NAME/KEY: SITE
<222> LOCATION: (1)..(246)
<223> OTHER INFORMATION: amino acid of PflA from strain DD1

<400> SEQUENCE: 11

Met Ser Val Leu Gly Arg Ile His Ser Phe Glu Thr Cys Gly Thr Val
1               5                   10                  15

Asp Gly Pro Gly Ile Arg Phe Ile Leu Phe Leu Gln Gly Cys Leu Met
            20                  25                  30

Arg Cys Lys Tyr Cys His Asn Arg Asp Thr Trp Asp Leu His Gly Gly
        35                  40                  45

Lys Glu Ile Ser Val Glu Glu Leu Met Lys Glu Val Val Thr Tyr Arg
    50                  55                  60

His Phe Met Asn Ala Ser Gly Gly Gly Val Thr Ala Ser Gly Gly Glu
65                  70                  75                  80
```

```
Ala Ile Leu Gln Ala Glu Phe Val Arg Asp Trp Phe Arg Ala Cys His
             85                  90                  95

Lys Glu Gly Ile Asn Thr Cys Leu Asp Thr Asn Gly Phe Val Arg His
            100                 105                 110

His Asp His Ile Ile Asp Glu Leu Ile Asp Thr Asp Leu Val Leu
        115                 120                 125

Leu Asp Leu Lys Glu Met Asn Glu Arg Val His Glu Ser Leu Ile Gly
130                 135                 140

Val Pro Asn Lys Arg Val Leu Glu Phe Ala Lys Tyr Leu Ala Asp Arg
145                 150                 155                 160

Asn Gln Arg Thr Trp Ile Arg His Val Val Pro Gly Tyr Thr Asp
                165                 170                 175

Ser Asp Glu Asp Leu His Met Leu Gly Asn Phe Ile Lys Asp Met Lys
                180                 185                 190

Asn Ile Glu Lys Val Glu Leu Leu Pro Tyr His Arg Leu Gly Ala His
            195                 200                 205

Lys Trp Glu Val Leu Gly Asp Lys Tyr Glu Leu Glu Asp Val Lys Pro
210                 215                 220

Pro Thr Lys Glu Leu Met Glu His Val Lys Gly Leu Leu Ala Gly Tyr
225                 230                 235                 240

Gly Leu Asn Val Thr Tyr
                245

<210> SEQ ID NO 12
<211> LENGTH: 2313
<212> TYPE: DNA
<213> ORGANISM: Basfia succiniciproducens
<220> FEATURE:
<221> NAME/KEY: misc_feature
<223> OTHER INFORMATION: nucleotide sequence of pflD-gene from strain
      DD1

<400> SEQUENCE: 12
atggctgaat taacagaagc tcaaaaaaaa gcatgggaag gattcgttcc cggtgaatgg      60
caaaacggcg taaatttacg tgactttatc caaaaaaact atactccgta tgaaggtgac    120
gaatcattct tagctgatgc gactcctgca accagcgagt tgtggaacag cgtgatggaa    180
ggcatcaaaa tcgaaaacaa aactcacgca cctttagatt cgacgaaca tactccgtca    240 actatcactt ctcacaagcc tggttatatc aataaagatt tagaaaaaat cgttggtctt    300
caaacagacg ctccgttaaa acgtgcaatt atgccgtacg gcggtatcaa aatgatcaaa    360
ggttcttgcg aagtttacgg tcgtaaatta gatccgcaag tagaatttat tttcaccgaa    420
tatcgtaaaa cccataacca aggcgtattc gacgtttata cgccggatat tttacgctgc    480
cgtaaatcag gcgtgttaac cggtttaccg gatgcttacg tcgtggtcg tattatcggt    540 gactaccgtc gtttagcggt atacggtatt gattacctga tgaaagataa aaaagcccaa    600
ttcgattcat tacaaccgcg tttggaagcg gcgaagaca ttcaggcaac tatccaatta    660
cgtgaagaaa ttgccgaaca cacccgcgct ttaggcaaaa tcaaagaaat ggcggcatct    720
tacggttacg acatttccgg ccctgcgaca aacgcacagg aagcaatcca atggacatat    780
tttgcttatc tggcagcggt taaatcacaa acggtgcgg caatgtcatt cggtcgtacg    840
tctacattct tagatatcta tatcgaacgt gacttaaaac gcggtttaat cactgaacaa    900
caggcgcagg aattaatgga ccacttagta atgaaattac gtatggttcg tttcttacgt    960
acgccggaat acgatcaatt attctcaggc gacccgatgt gggcaaccga aactatcgcc   1020
```

```
ggtatgggct tagacggtcg tccgttggta actaaaaaca gcttccgcgt attacatact    1080
ttatacacta tgggtacttc tccggaacca aacttaacta ttctttggtc cgaacaatta    1140
cctgaagcgt tcaaacgttt ctgtgcgaaa gtatctattg atacttcctc cgtacaatac    1200
gaaaatgatg acttaatgcg tcctgacttc aacaacgatg actatgcaat cgcatgctgc    1260
gtatcaccga tggtcgtagg taaacaaatg caattcttcg gtgcgcgcgc aaacttagct    1320
aaaactatgt tatacgcaat taacggcggt atcgatgaga aaaatggtat gcaagtcggt    1380
cctaaaactg cgccgattac agacgaagta ttgaatttcg ataccgtaat cgaacgtatg    1440
gacagtttca tggactggtt ggcgactcaa tatgtaaccg cattgaacat catccacttc    1500
atgcacgata aatatgcata tgaagcggca ttgatggcgt ccacgatcg cgacgtattc     1560 cgtacaatgg cttgcggtat cgcgggtctt tccgtggctg cggactcatt atccgcaatc    1620
aaatatgcga agttaaaacc gattcgcggc gacatcaaag ataaagacgg taatgtcgtg    1680
gcctcgaatg ttgctatcga cttcgaaatt gaaggcgaat atccgcaatt cggtaacaat    1740
gatccgcgtg ttgatgattt agcggtagac ttagttgaac gtttcatgaa aaaagttcaa    1800
aaacacaaaa cttaccgcaa cgcaactccg acacaatcta tcctgactat cacttctaac    1860
gtggtatacg gtaagaaaac cggtaatact ccggacggtc gtcgagcagg cgcgccattc    1920
ggaccgggtg caaacccaat gcacggtcgt gaccaaaaag gtgcggttgc ttcacttact    1980
tctgtggcta aacttccgtt cgcttacgcg aaagacggta tttcatatac cttctctatc    2040
gtaccgaacg cattaggtaa agatgacgaa gcgcaaaaac gcaaccttgc cggtttaatg    2100
gacggttatt ccatcatga agcgacagtg gaaggcggtc aacacttgaa tgttaacgtt    2160
cttaaccgtg aaatgttgtt agacgcgatg gaaaatccgg aaaaatacc gcaattaacc     2220 attcgtgttt caggttacgc ggttcgtttc aactcattaa ctaaagagca acaacaagac    2280
gtcatcactc gtacgtttac acaatcaatg taa                                 2313
```

<210> SEQ ID NO 13
<211> LENGTH: 770
<212> TYPE: PRT
<213> ORGANISM: Basfia succiniciproducens
<220> FEATURE:
<221> NAME/KEY: SITE
<222> LOCATION: (1)..(770)
<223> OTHER INFORMATION: amino acid of PflD from strain DD1

<400> SEQUENCE: 13

```
Met Ala Glu Leu Thr Glu Ala Gln Lys Lys Ala Trp Glu Gly Phe Val
1               5                   10                  15

Pro Gly Glu Trp Gln Asn Gly Val Asn Leu Arg Asp Phe Ile Gln Lys
            20                  25                  30

Asn Tyr Thr Pro Tyr Glu Gly Asp Glu Ser Phe Leu Ala Asp Ala Thr
        35                  40                  45

Pro Ala Thr Ser Glu Leu Trp Asn Ser Val Met Glu Gly Ile Lys Ile
    50                  55                  60

Glu Asn Lys Thr His Ala Pro Leu Asp Phe Asp Glu His Thr Pro Ser
65                  70                  75                  80

Thr Ile Thr Ser His Lys Pro Gly Tyr Ile Asn Lys Asp Leu Glu Lys
                85                  90                  95

Ile Val Gly Leu Gln Thr Asp Ala Pro Leu Lys Arg Ala Ile Met Pro
            100                 105                 110

Tyr Gly Gly Ile Lys Met Ile Lys Gly Ser Cys Glu Val Tyr Gly Arg
        115                 120                 125
```

```
Lys Leu Asp Pro Gln Val Glu Phe Ile Phe Thr Glu Tyr Arg Lys Thr
    130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Leu Ala Val Tyr Gly Ile Asp Tyr
            180                 185                 190

Leu Met Lys Asp Lys Lys Ala Gln Phe Asp Ser Leu Gln Pro Arg Leu
        195                 200                 205

Glu Ala Gly Glu Asp Ile Gln Ala Thr Ile Gln Leu Arg Glu Glu Ile
    210                 215                 220

Ala Glu Gln His Arg Ala Leu Gly Lys Ile Lys Glu Met Ala Ala Ser
225                 230                 235                 240

Tyr Gly Tyr Asp Ile Ser Gly Pro Ala Thr Asn Ala Gln Glu Ala Ile
                245                 250                 255

Gln Trp Thr Tyr Phe Ala Tyr Leu Ala Ala Val Lys Ser Gln Asn Gly
            260                 265                 270

Ala Ala Met Ser Phe Gly Arg Thr Ser Thr Phe Leu Asp Ile Tyr Ile
        275                 280                 285

Glu Arg Asp Leu Lys Arg Gly Leu Ile Thr Glu Gln Gln Ala Gln Glu
    290                 295                 300

Leu Met Asp His Leu Val Met Lys Leu Arg Met Val Arg Phe Leu Arg
305                 310                 315                 320

Thr Pro Glu Tyr Asp Gln Leu Phe Ser Gly Asp Pro Met Trp Ala Thr
                325                 330                 335

Glu Thr Ile Ala Gly Met Gly Leu Asp Gly Arg Pro Leu Val Thr Lys
            340                 345                 350

Asn Ser Phe Arg Val Leu His Thr Leu Tyr Thr Met Gly Thr Ser Pro
        355                 360                 365

Glu Pro Asn Leu Thr Ile Leu Trp Ser Glu Gln Leu Pro Glu Ala Phe
    370                 375                 380

Lys Arg Phe Cys Ala Lys Val Ser Ile Asp Thr Ser Ser Val Gln Tyr
385                 390                 395                 400

Glu Asn Asp Asp Leu Met Arg Pro Asp Phe Asn Asn Asp Asp Tyr Ala
                405                 410                 415

Ile Ala Cys Cys Val Ser Pro Met Val Val Gly Lys Gln Met Gln Phe
            420                 425                 430

Phe Gly Ala Arg Ala Asn Leu Ala Lys Thr Met Leu Tyr Ala Ile Asn
        435                 440                 445

Gly Gly Ile Asp Glu Lys Asn Gly Met Gln Val Gly Pro Lys Thr Ala
    450                 455                 460

Pro Ile Thr Asp Glu Val Leu Asn Phe Asp Thr Val Ile Glu Arg Met
465                 470                 475                 480

Asp Ser Phe Met Asp Trp Leu Ala Thr Gln Tyr Val Thr Ala Leu Asn
                485                 490                 495

Ile Ile His Phe Met His Asp Lys Tyr Ala Tyr Glu Ala Ala Leu Met
            500                 505                 510

Ala Phe His Asp Arg Asp Val Phe Arg Thr Met Ala Cys Gly Ile Ala
        515                 520                 525

Gly Leu Ser Val Ala Ala Asp Ser Leu Ser Ala Ile Lys Tyr Ala Lys
    530                 535                 540
```

```
Val Lys Pro Ile Arg Gly Asp Ile Lys Asp Lys Asp Gly Asn Val Val
545                 550                 555                 560

Ala Ser Asn Val Ala Ile Asp Phe Glu Ile Glu Gly Glu Tyr Pro Gln
                565                 570                 575

Phe Gly Asn Asn Asp Pro Arg Val Asp Asp Leu Ala Val Asp Leu Val
            580                 585                 590

Glu Arg Phe Met Lys Lys Val Gln Lys His Lys Thr Tyr Arg Asn Ala
        595                 600                 605

Thr Pro Thr Gln Ser Ile Leu Thr Ile Thr Ser Asn Val Val Tyr Gly
    610                 615                 620

Lys Lys Thr Gly Asn Thr Pro Asp Gly Arg Arg Ala Gly Ala Pro Phe
625                 630                 635                 640

Gly Pro Gly Ala Asn Pro Met His Gly Arg Asp Gln Lys Gly Ala Val
                645                 650                 655

Ala Ser Leu Thr Ser Val Ala Lys Leu Pro Phe Ala Tyr Ala Lys Asp
            660                 665                 670

Gly Ile Ser Tyr Thr Phe Ser Ile Val Pro Asn Ala Leu Gly Lys Asp
        675                 680                 685

Asp Glu Ala Gln Lys Arg Asn Leu Ala Gly Leu Met Asp Gly Tyr Phe
    690                 695                 700

His His Glu Ala Thr Val Gly Gly Gln His Leu Asn Val Asn Val
705                 710                 715                 720

Leu Asn Arg Glu Met Leu Leu Asp Ala Met Glu Asn Pro Glu Lys Tyr
                725                 730                 735

Pro Gln Leu Thr Ile Arg Val Ser Gly Tyr Ala Val Arg Phe Asn Ser
            740                 745                 750

Leu Thr Lys Glu Gln Gln Gln Asp Val Ile Thr Arg Thr Phe Thr Gln
        755                 760                 765

Ser Met
    770

<210> SEQ ID NO 14
<211> LENGTH: 30
<212> TYPE: DNA
<213> ORGANISM: artificial sequence
<220> FEATURE:
<223> OTHER INFORMATION: nucleotide sequence of primer PRfruA1

<400> SEQUENCE: 14
tgctctagat gcggaagaga gcctttccgg                                        30

<210> SEQ ID NO 15
<211> LENGTH: 64
<212> TYPE: DNA
<213> ORGANISM: artificial sequence
<220> FEATURE:
<223> OTHER INFORMATION: nucleotide sequence of primer PRfruA2

<400> SEQUENCE: 15
caccaggttt tggctgccgc agtaaaacaa tttcctaatc aagcataaag cctttgttta      60
tctc                                                                   64

<210> SEQ ID NO 16
<211> LENGTH: 64
<212> TYPE: DNA
<213> ORGANISM: artificial sequence
<220> FEATURE:
<223> OTHER INFORMATION: nucleotide sequence of primer PRfruA3
```

```
<400> SEQUENCE: 16
gagataaaca aaggctttat gcttgattag gaaattgttt tactgcggca gccaaaacct    60
ggtg                                                                 64

<210> SEQ ID NO 17
<211> LENGTH: 35
<212> TYPE: DNA
<213> ORGANISM: artificial sequence
<220> FEATURE:
<223> OTHER INFORMATION: nucleotide sequence of primer PRfruA4

<400> SEQUENCE: 17
ccgctcgagt aggagtaact caaggtcacc gtttg                               35

<210> SEQ ID NO 18
<211> LENGTH: 34
<212> TYPE: DNA
<213> ORGANISM: artificial sequence
<220> FEATURE:
<223> OTHER INFORMATION: nucleotide sequence of primer PRrbsK1

<400> SEQUENCE: 18
ggcggccgct ctagaccgaa tatttctgcc ccgc                                34

<210> SEQ ID NO 19
<211> LENGTH: 42
<212> TYPE: DNA
<213> ORGANISM: artificial sequence
<220> FEATURE:
<223> OTHER INFORMATION: nucleotide sequence of primer PRrbsK2

<400> SEQUENCE: 19
gtttgtcata tgcattgaac gaatagacgt ttgggaatgt ta                       42

<210> SEQ ID NO 20
<211> LENGTH: 46
<212> TYPE: DNA
<213> ORGANISM: artificial sequence
<220> FEATURE:
<223> OTHER INFORMATION: nucleotide sequence of primer PRrbsK3

<400> SEQUENCE: 20
acgtctattc gttcaatgca tatgacaaac aaaatttggg tattag                   46

<210> SEQ ID NO 21
<211> LENGTH: 39
<212> TYPE: DNA
<213> ORGANISM: artificial sequence
<220> FEATURE:
<223> OTHER INFORMATION: nucleotide sequence of primer PRrbsK4

<400> SEQUENCE: 21
gggcccgccc tcgagcctag cttaaagata gccggtaaa                           39

<210> SEQ ID NO 22
<211> LENGTH: 9517
<212> TYPE: DNA
<213> ORGANISM: artificial sequence
<220> FEATURE:
<223> OTHER INFORMATION: nucleotide sequence of plasmid
      pJFF224_PackArbsK

<400> SEQUENCE: 22
ccccggagtg gttcgacggc ctcaagcgcg ccgccgaggg ccgccgcctg atggtgctgg    60
```

-continued

```
acacgctgcg ccggttccac atcgaggaag aaaacgccag cggccccatg cccaggtca     120 tcggtcgcat ggaggccatc gccgccgata ccgggtgctc tatcgtgttc ctgcaccatg    180
ccagcaaggg cgcggccatg atgggcgcag gcgaccagca gcaggccagc cggggcagct    240
cggtactggt cgataacatc cgctggcagt cctacctgtc gagcatgacc agcgccgagg    300
ccgaggaatg gggtgtggac gacgaccagc gccggttctt cgtccgcttc ggtgtgagca    360
aggccaacta tggcgcaccg ttcgctgatc ggtggttcag gcggcatgac ggcggggtgc    420
tcaagcccgc cgtgctggag aggcagcgca agagcaaggg ggtgccccgt ggtgaagcct    480
aagaacaagc acagcctcag ccacgtccgg cacgacccgg cgcactgtct ggccccccggc   540 ctgttccgtg ccctcaagcg gggcgagcgc aagcgcagca agctggacgt gacgtatgac    600
tacggcgacg gcaagcggat cgagttcagc ggccccgagc cgctgggcgc tgatgatctg    660
cgcatcctgc aagggctggt ggccatggct gggcctaatg gcctagtgct tggcccggaa    720
cccaagaccg aaggcggacg gcagctccgg ctgttcctgg aacccaagtg ggaggccgtc    780
accgctgatg ccatggtggt caaaggtagc tatcgggcgc tggcaaagga aatcggggca    840
gaggtcgata gtggtggggc gctcaagcac atacaggact gcatcgagcg cctttggaag    900
gtatccatca tcgcccagaa tggccgcaag cggcaggggt tcggctgct gtcggagtac     960 gccagcgacg aggcggacgg gcgcctgtac gtggccctga cccccttgat cgcgcaggcc   1020
gtcatgggtg gcgccagca tgtgcgcatc agcatggacg aggtgcgggc gctggacagc   1080
gaaaccgccc gcctgctgca ccagcggctg tgtggctgga tcgacccgg caaaaccggc    1140 aaggcttcca tagataccct tgtgcggctat gtctggccgt cagaggccag tggttcgacc   1200
atgcgcaagc gccgccagcg ggtgcgcgag gcgttgccgg agctggtcgc gctgggctgg   1260
acggtaaccg agttcgcggc gggcaagtac gacatcaccc ggcccaaggc ggcaggctga   1320
ccccccccac tctattgtaa acaagacatt ttttatcttt tatattcaat ggcttatttt    1380
cctgctaatt ggtaatacca tgaaaaatac catgctcaga aaaggcttaa caatattttg    1440
aaaaattgcc tactgagcgc tgccgcacag ctccataggc cgcttttcctg gctttgcttc    1500 cagatgtatc tctcctccg gagagtaccg tgactttatt ttcggcacaa atacaggggt    1560
cgatggataa atacggcgat agtttcctga cggatgatcc gtatgtaccg gcggaagaca   1620
agctgcaaac ctgtcagatg gagattgatt taatggcgga tgtgctgaga gcaccgcccc   1680
gtgaatccgc agaactgatc cgctatgtgt ttgcggatga ttggccggaa taaataaagc    1740
cgggcttaat acagattaag cccgtatagg gtattattac tgaataccaa acagcttacg   1800
gaggacggaa tgttacccat tgagacaacc agactgcctt ctgattatta atattttca     1860 ctattaatca gaaggaataa ccatgaattt taccccggatt gacctgaata cctggaatcg   1920
cagggaacac tttgcccttt atcgtcagca gattaaatgc ggattcagcc tgaccaccaa    1980
actcgatatt accgctttgc gtaccgcact ggcggagaca ggttataagt tttatccgct    2040
gatgatttac ctgatctccc gggctgttaa tcagtttccg gagttccgga tggcactgaa    2100
agacaatgaa cttatttact gggaccagtc agacccggtc tttactgtct ttcataaaga    2160
aaccgaaaca ttctctgcac tgtcctgccg ttatttccg gatctcagtg agtttatggc    2220
aggttataat gcggtaacgg cagaatatca gcatgatacc agattgtttc gcagggaaa    2280 tttaccggag aatcacctga atatatcatc attaccgtgg gtgagttttg acgggattta   2340
acctgaacat caccggaaat gatgattatt ttgccccggt ttttacgatg gcaaagtttc   2400
agcaggaagg tgaccgcgta ttattacctg tttctgtaca ggttcatcat gcagtctgtg    2460
```

```
atggctttca tgcagcacgg tttattaata cacttcagct gatgtgtgat aacatactga    2520
aataaattaa ttaattctgt atttaagcca ccgtatccgg caggaatggt ggcttttttt    2580
ttatatttta accgtaatct gtaatttcgt ttcagactgg ttcaggatca ctgtacgata    2640
atgcccccgc agtttggtaa taccctaat aaaaaagaaa cagcaaagac tgacagcaat    2700
aataataaag taagcagtaa caataatatt aacaacacca gatgcagtta taataatagt    2760
atttaagaca ccagaaagac tgctgcgaca gtcattttga acaacaccaa aatgccgtaa    2820
aggcagtagt aacaacacca gtgaaaacat cacgatagca tagtgatatg cctgagtgtg    2880
tgtaattaaa caataaataa accgccatat ataacagaag atagtattct gaatggcatg    2940
cttttctgtt cagtataaac atatcatccc ggttggtata aggatgatat ataataagtt    3000
aagctgaaca catatttatt ttggttttat tttacaaata aagtaagacg atccgttaag    3060
tcaaagcggg gtatatttat tataccctgc ttttttattt gtccgccggg cgcggataat    3120
ggatcagatt atgcagtgtc acaatggcct taccgggatt ggcgtaagcg tgcgggatat    3180
ccgcatggaa gcgcagggat tccccggcag aaacggtgtg ccactcatcc cccagccgca    3240
gttgtaatgc gccttccagt acaatgacat gttctctggt tctgaaatcc atccctgtcg    3300
gtgttgctta tgcagtctgg tcgggactcg gcgtcgtcat aattacagcc attgcctggt    3360
tgcttcatgg gcaaaagctt tatgcttgta aaccgttttg tgaaaaaatt tttaaaataa    3420
aaaaggggac ctctagggtc cccaattaat tagtaatata atctattaaa ggtcattcaa    3480
aaggtcatcc accggatccc accgcggtgg cggccgctct agaccgaata tttctgcccc    3540
gccgatatag ttttaaaaaa tcccattttt aaatccttaa tttatatttc ttcaaatttt    3600
tactactgac ttattttaaa tttgctgcca ttttatcctg tttttaaagat cgcttatcgc    3660 atgaaactca aatggcttat tggatatatg tcctaaaaat tgaacatttt tataacattt    3720
tgctaaaaat tcaattttt ttgacttaaa tcgcttttt cagaacttca taatttattt    3780
tattccgtta aacgtgtatc cttattatcg gtaacattcc caaacgtcta ttcgttcaat    3840
gcatatgaca aacaaaattt gggtattagg cgatgccgtg gtggattaaa ttcctgacgg    3900
agacaaccat tatttgcgtt gcgcaggcgg cgcaccggct aatgtggcgg tcggcgttgc    3960
ccgtttaggt gtgcctagcg catttatcgg ccgtgtaggt aaagatccgt taggggaatt    4020
tatgcgcgat acgctgaatc aggaaaatgt aaacaccgat tatatgttgt tagatcctaa    4080
acaacgtact tcgacggtgg tggttggatt aaccgacggc gaacgtagtt ttacctttat    4140
ggtgaatcca agtgcggatc aattttttaca aatttccgat ctgccgcaat ttcaagccgg    4200
agactggttg cactgctgct ctatcgcctt aatcaatgaa ccgacccgca gcgctacttt    4260
cacggcaatg aaaaatatcc gtgcggccgg cggtaaagta tctttcgatc cgaatttacg    4320
cgaaagctta tggaaatccc aggatgaaat gatcgatgtg gtgatggaag cggtaagcct    4380
tgccgacgta ttgaaatttt cagaagaaga attaacgctg ttaacccata ccgacagcct    4440
ggaaaaatct tttgaaaaaa tcaccgcact ttatcccgat aaattgatta ttgtcacttt    4500
agggaaagat ggcgcgctct atcatctgca cggtaaaaaa gaggtggttg cagggaaagc    4560
gctgaaaccg gtagatacca ccggtgccgg cgacgctttt gtcagcgggt tattagccgg    4620
attatcacaa acggaaaact ggcagcaacc tgaacaactc gttactatta ttcgccaggc    4680
caacgccagc ggcgcgcttg ccacaacggc aaaaggcgct atgtcggcat taccgaatcg    4740
gcaacaatta gcggaatttt tagcaaacta aaattcgcaa aatttattcc aaactcattc    4800
```

```
tccgattatt aattgcatca acttaaaaag taaaaatgca gtgcgttaag cggcctatgt    4860
gagtgttccg ctaaatctgc acgaattaaa gaacgtttat atgcccctaa tcggcaggtt    4920
atatccattg attagtacag tacaaaaaag tccggcgctt atcaccggac tttttatgc     4980 ctaaaaatag aatttggtat aaatatattg ttttttatat ttaccggcta tctttaagct    5040
aggctcgagg gggggcccgg atccccagta gatttacgtt taaacatttt tatttccttt    5100
ttaatttaat ttaattaaca gttggtgcta tgacacttta cctcatagct ggcataattc    5160
gcaatactct gggtcttcga gaggtatcca acctgagttg aaatacttta ccatcgattt    5220
agcagttgta tcagttatat ttatattacc tttaactctt cgccatccag gagttttacc    5280
gtacagatta gaggataata ataacacata attctcgtaa gcaatatgag ataatttcca    5340
agactctata ttagctcgtg atgttttcca aggtctaaaa tcgtcacggt tcatataatt    5400
agccaatctc atatgctctc taacttccga tgataagctg tcaaacatga gaattaacga    5460
tctgatagag aagggtttgc tcgggtcggt ggctctggta acgaccagta tcccgatccc    5520
ggctggccgt cctggccgcc acatgaggca tgttccgcgt ccttgcaata ctgtgtttac    5580
atacagtcta tcgcttagcg gaaagttctt ttaccctcag ccgaaatgcc tgccgttgct    5640
agacattgcc agccagtgcc cgtcactccc gtactaactg tcacgaaccc ctgcaataac    5700
tgtcacgccc cctgcaata actgtcacga accctgcaa taactgtcac gccccaaac     5760 ctgcaaaccc agcaggggcg ggggctggcg gggtgttgga aaaatccatc catgattatc    5820
taagaataat ccactaggcg cggttatcag cgcccttgtg gggcgctgct gcccttgccc    5880
aatatgcccg gccagaggcc ggatagctgg tctattcgct cgctaggct acacaccgcc     5940 ccaccgctgc gcggcagggg gaaaggcggg caaagcccgc taaaccccac accaaacccc    6000
gcagaaatac gctgggagcg cttttagccg ctttagcggc cttttccccct acccgaaggg    6060 tggggcgcg tgtgcagccc cgcagggcct gtctcggtcg atcattcagc ccggctcatc     6120
cttctggcgt ggcggcagac cgaacaaggc gcggtcgtgg tcgcgttcaa ggtacgcatc    6180
cattgccgcc atgagccgat cctccggcca ctcgctgctg ttcaccttgg ccaaaatcat    6240 ggccccacc agcaccttgc gccttgtttc gttcttgcgc tattgctgct gttcccttgc     6300
ccgcacccgc tgaatttcgg cattgattcg cgctcgttgt tcttcgagct tggccagccg    6360 atccgccgc ttgttgctcc ccttaaccat cttgacaccc cattgttaat gtgctgtctc     6420
gtaggctatc atggaggcac agcggcggca atcccgaccc tactttgtag gggagggcca    6480
ttgcatggag ccgaaaagca aaagcaacag cgaggcagca tggcgattta tcaccttacg    6540
gcgaaaaccg gcagcaggtc gggcggccaa tcggccaggg ccaaggccga ctacatccag    6600
cgcgaaggca agtatgcccg cgacatggat gaagtcttgc acgccgaatc cgggcacatg    6660
ccggagttcg tcgagcggcc cgccgactac tgggatgctg ccgacctgta tgaacgcgcc    6720
aatgggcggc tgttcaagga ggtcgaattt gccctgccgg tcgagctgac cctcgaccag    6780
cagaaggcgc tggcgtccga gttcgcccag cacctgaccg gtgccgagcg cctgccgtat    6840
acgctggcca tccatgccgg tggcggcgag aacccgcact gccacctgat gatctccgag    6900
cggatcaatg acggcatcga gcggcccgcc gctcagtggt tcaagcggta caacggcaag    6960
accccggaga agggcggggc acagaagacc gaagcgctca gcccaaggc atggcttgag     7020 cagacccgcg aggcatgggc cgaccatgcc aacggcat tagagcgggc tggccacgac    7080
gcccgcattg accacagaac acttgaggcg caggcatcg agcgcctgcc cggtgttcac    7140
ctggggccga acgtggtgga gatggaaggc cggggcatcc gcaccgaccg gcagacgtg     7200
```

```
gccctgaaca tcgacaccgc caacgcccag atcatcgact acaggaata ccggaggca    7260 atagaccatg aacgcaatcg acagagtgaa gaaatccaga ggcatcaacg agttagcgga   7320
gcagatcgaa ccgctggccc agagcatggc gacactggcc gacgaagccc ggcaggtcat   7380
gagccagacc cagcaggcca gcgaggcgca ggcggcggag tggctgaaag cccagcgcca   7440
gacaggggcg gcatgggtgg agctggccaa agagttgcgg gaggtagccg ccgaggtgag   7500
cagcgccgcg cagagcgccc ggagcgcgtc gcggggggtgg cactggaagc tatggctaac  7560
cgtgatgctg gcttccatga tgcctacggt ggtgctgctg atcgcatcgt tgctcttgct   7620
cgacctgacg ccactgacaa ccgaggacgg ctcgatctgg ctgcgcttgg tggcccgatg   7680
aagaacgaca ggactttgca ggccataggc cgacagctca aggccatggg ctgtgagcgc   7740
ttcgatatcg gcgtcaggga cgccaccacc ggccagatga tgaaccggga atggtcagcc   7800
gccgaagtgc tccagaacac gccatggctc aagcggatga atgcccaggg caatgacgtg   7860
tatatcaggc ccgccgagca ggagcggcat ggtctggtgc tggtggacga cctcagcgag   7920
tttgacctgg atgacatgaa agccgagggc cgggagcctg ccctggtagt ggaaaccagc   7980
ccgaagaact atcaggcatg ggtcaaggtg gccgacgccg caggcggtga acttcggggg   8040
cagattgccc ggacgctggc cagcgagtac gacgccgacc cggccagcgc cgacagccgc   8100
cactatggcc gcttggcggg cttcaccaac cgcaaggaca agcacaccac ccgcgccggt   8160
tatcagccgt gggtgctgct gcgtgaatcc aagggcaaga ccgccaccgc tggcccggcg   8220
ctggtgcagc aggctggcca gcagatcgag caggcccagc ggcagcagga gaaggcccgc   8280
aggctggcca gcctcgaact gcccgagcgg cagcttagcc gccaccggcg cacggcgctg   8340
gacgagtacc gcagcgagat ggccgggctg gtcaagcgct tcggtgatga cctcagcaag   8400
tgcgacttta tcgccgcgca gaagctggcc agccggggcc gcagtgccga ggaaatcggc   8460
aaggccatgg ccgaggccag cccagcgctg gcagagcgca agcccggcca cgaagcggat   8520
tacatcgagc gcaccgtcag caaggtcatg ggtctgccca gcgtccagct tgcgcgggcc   8580
gagctggcac gggcaccggc accccgccag cgaggcatgg acaggggcgg gccagatttc   8640
agcatgtagt gcttgcgttg gtactcacgc ctgttatact atgagtactc acgcacagaa   8700 ggggggtttta tggaatacga aaaaagcgct tcagggtcgg tctacctgat caaaagtgac   8760
aagggctatt ggttgcccgg tggctttggt tatacgtcaa acaaggccga ggctggccgc   8820
ttttcagtcg ctgatatggc cagccttaac cttgacggct gcaccttgtc cttgttccgc   8880
gaagacaagc ctttcggccc cggcaagttt ctcggtgact gatatgaaag accaaaagga   8940
caagcagacc ggcgacctgc tggccagccc tgacgctgta cgccaagcgc gatatgccga   9000
gcgcatgaag gccaagggga tgcgtcagcg caagttctgg ctgaccgacg acgaatacga   9060
ggcgctgcgc gagtgcctgg aagaactcag agcggcgcag ggcgggggta gtgaccccgc   9120
cagcgcctaa ccaccaactg cctgcaaagg aggcaatcaa tggctaccca taagcctatc   9180
aatattctgg aggcgttcgc agcagcgccg ccaccgctgg actacgttttt gcccaacatg   9240 gtggccggta cggtcgggc gctggtgtcg cccggtggtg ccggtaaatc catgctggcc   9300
ctgcaactgg ccgcacagat tgcaggcggg ccggatctgc tggaggtggg cgaactgccc   9360
accggcccgg tgatctacct gcccgccgaa gacccgccca ccgccattca tcaccgcctg   9420
cacgcccttg gggcgcacct cagcgccgag gaacggcaag ccgtggctga cggcctgctg   9480
atccagccgc tgatcggcag cctgcccaac atcatgg                           9517
```

<210> SEQ ID NO 23
<211> LENGTH: 7183
<212> TYPE: DNA
<213> ORGANISM: artificial sequence
<220> FEATURE:
<223> OTHER INFORMATION: nucleotide sequence of plasmid
      pClikCM_delta_fruA

<400> SEQUENCE: 23

```
tcgagtagga gtaactcaag gtcaccgttt gcgttttgtt gccgaaggtg cgcaggcaca      60
gcaggcgatt gaagccatcg ctaaagaaat tgcggcgggc ttgggtgagc ctgtttccgc     120
cgttccgccg gcagaaccgg atactattga agtcgctaac ccggcgacac cggaagttga     180
gcaaccaaaa tccgacagta tcgaagcggt ttttgtgatt aataatgaaa acggtctgca     240
tgctcgtcct gcgcgactt tagtgaatga agtcaaaaaa tataatgcgt cggtggcggt     300
tcgtaattta gatcgcgacg gtgggttagt gagcgctaaa agcatgatga aaatcgttgc     360
attaggtgcg acaaaaggtt ctcgtctgca ttttgtcgcc accggtgaag aagctcaaca     420
agcgattgac ggtatcggtg cggcaatcgc ggcaggttta ggagaataaa caatggcaaa     480
agtggcaaca attacattaa acgccgccta tgatttggtc gggcgtttaa aacgcattga     540
attgggcgaa gtgaatacgg tggaaaccct cggtttattc cctgccggta aaggtatcaa     600
tgtggctaag gtgttgaatg acttagatgt tgaagtcgcg gtcggtggtt ttctcggtga     660
agataacgta ggcgatttcg agcatttatt ccaacaacaa ggtttgcagg ataaattcca     720
gcgggttgcc ggtaaaaccc gaataaacgt aaaaatcacc gaaacggacg cggatgtaac     780
ggatttgaat tttcttggtt atcaaatcag tgaacaggat tggcggaaat ttaccgcaga     840
ttctctcgct tattgtaaag aattcgacat cgttgccgtg tgtggcagtt tgccccgcgg     900
cgtaacggcg gatatgtttc aaagctggtt aagtcaatta catcaagcgg gtgtaaaagt     960
cgtactagat agtagtaatg ccgcattaac agcaggtctt aaagcaaatc cttggttagt    1020
gaaaccgaat caccgcgaat tagaagcctg ggtcggccat gagttaccga cttttgaaga    1080
catcattgac gccgcaaaac aattaaaagc acaagggata gccaatgtta ttatttccat    1140
gggcgcaaac ggctcattat ggctaagtga taacggcgtg attttggctc agccgccgaa    1200
atgtgaaaac gtagtaagca gtcggtgc cggcgattcg atggtcgcag gtttaattta    1260
tggttttgta ataatttat ctcaacaaga aacattggcg tttgcaagtg cggtatctgc    1320
cttcgccgtt tcacaaagta acgtaggtgt cagtgatcgc aagttgctcg acccaatctt    1380
agcaaatgta aaaatcacaa cgattgaagg ataagccgat gaatattttt cttacgcaat    1440
caccaaattt aggtcgtgca aaagcgtttt tattgcacca ggttttggct gccgcagtaa    1500
aacaatttcc taatcaagca taagcctttt gtttatctca aaacaaaggc ttttttttata    1560
agtattccgc tttgcccgaa ctaatagaaa aattggcaga caaagaagt gttcatagca    1620
caggaggaac aatatggatt tcaatgcaat tttaaatcaa gttttaagtg ccgctcagga    1680
aaccgttaag aaaacggcaa gcggcaatag cacaacggat aaagtggcaa aaatcggtgg    1740
cggtgcagcg gctatcggcg tgcttttcgat gattttcggg cgcaccggcg gagcggggct    1800
tgcaaaatta ggctcgcttg ccgcattagg cagccttgct tatcaggctt accaggatta    1860
tcaacataaa caaagccaag ttgtaccggt tactgaaacg gaatttaccc aaagcgtaca    1920
acaatcggcg gaactcagca agtgattttt gcaggcaatg attgcggcgg cggctgcaga    1980
cggcgcgatt tccgaccagg aacaacaagc gattttaagc caagccggcg atgatgcgga    2040
```

```
agtacagcag tggattcggc aagaaatgta tcaaccggca acagtgcggg aaatcgccca    2100
acaagtgggt gataatcagg cattagcatc acaggtgtat ctggcggcaa gaatggtttg    2160
cgccgattta gcacgcaaag aaattgtttt cttagcaaat ttagcgcaag cgttggggtt    2220
agatgaagcg cttgtagaac agttagaaaa acaggcgggt ttctgattta atcattccgc    2280
gatgtgcaaa gtgcggtcaa aaataacgat tttttaccg cacttttgca tttgcaagac    2340
gtttcgaaaa tgcctgttct aacttctatt aaaacccttc ttctaaaatt ttctccaata    2400
actcaaatac cagcaacact cgtttgggag taatggtttg ataaggacgg tagaggtaaa    2460
ttccccaaat caaggtttcc tcattagaga agactacttg taactcgccg gaatcaagat    2520
aggatttaca gtcatgatac attatcggcg cgaaaatcct gccggataag accgccggta    2580
acaagctttt aatatcgctg gtgataaccg tcggcttagt tagaattatg ggttgttcac    2640
ccatcatcca gtcccatact tgccggtcct taggatttaa aatatagcct accggaaaat    2700
tggcggctaa atcaaaaacg tcttttggca atccggtttt agcgataaga ctaggtgctg    2760
ccacgatagg ctcttgtagg tcagtaatct ttttcgccac ccaatgatct tcgggcgtgc    2820
ggctgatgcg aataccgata tcaatttggt catccaccgc tttgagcgta tcgaaatccg    2880
tgcgccagtc aatctgaata tccggatagg cgcaagtgc ggttagtaat cgcaataaaa    2940
ttttatccgc ataatcggaa ggcggtaacg taatccgcac taagccggaa aggctctctt    3000
ccgcatctag actccatagg ccgctttcct ggctttgctt ccagatgtat gctctcctcc    3060
ggagagtacc gtgactttat tttcggcaca aatacagggg tcgatggata aatacggcga    3120
tagtttcctg acgatgatc cgtatgtacc ggcggaagac aagctgcaaa cctgtcagat    3180
ggagattgat ttaatggcgg atgtgctgag agcaccgccc cgtgaatccg cagaactgat    3240
ccgctatgtg tttgcggatg attggccgga ataaataaag ccgggcttaa tacagattaa    3300
gcccgtatag ggtattatta ctgaatacca aacagcttac ggaggacgga atgttaccca    3360
ttgagacaac cagactgcct tctgattatt aatattttc actattaatc agaaggaata    3420
accatgaatt ttacccggat tgacctgaat acctggaatc gcagggaaca ctttgcccctt    3480 tatcgtcagc agattaaatg cggattcagc ctgaccacca aactcgatat taccgctttg    3540
cgtaccgcac tggcggagac aggttataag ttttatccgc tgatgattta cctgatctcc    3600
cgggctgtta atcagtttcc ggagttccgg atggcactga agacaatga acttatttac    3660 tgggaccagt cagacccggt ctttactgtc tttcataaag aaaccgaaac attctctgca    3720
ctgtcctgcc gttatttcc ggatctcagt gagtttatgg caggttataa tgcggtaacg    3780
gcagaatatc agcatgatac cagattgttt ccgcagggaa atttaccgga gaatcacctg    3840
aatatatcat cattaccgtg ggtgagtttt gacgggattt aacctgaaca tcaccggaaa    3900
tgatgattat tttgccccgg ttttacgat ggcaaagttt cagcaggaag gtgaccgcgt    3960
attattacct gtttctgtac aggttcatca tgcagtctgt gatggctttc atgcagcacg    4020
gtttattaat acacttcagc tgatgtgtga taacatactg aaataaatta attaattctg    4080
tatttaagcc accgtatccg gcaggaatgg tggctttttt tttatatttt aaccgtaatc    4140
tgtaatttcg tttcagactg gttcaggatg agctcgcttg gactcctgtt gatagatcca    4200
gtaatgacct cagaactcca tctggatttg ttcagaacgc tcggttgccg ccgggcgttt    4260 ttattggtg agaatccaag cactagcggc gcgccggccg gccccggtgtg aaataccgca    4320 cagatgcgta aggagaaaat accgcatcag gcgctcttcc gcttcctcgc tcactgactc    4380
gctgcgctcg gtcgttcggc tgcggcgagc ggtatcagct cactcaaagg cggtaatacg    4440
```

```
gttatccaca gaatcagggg ataacgcagg aaagaacatg tgagcaaaag gccagcaaaa    4500
ggccaggaac cgtaaaaagg ccgcgttgct ggcgttttc cataggctcc gccccctga     4560 cgagcatcac aaaaatcgac gctcaagtca gaggtggcga acccgacag gactataaag    4620 ataccaggcg tttccccctg gaagctccct cgtgcgctct cctgttccga ccctgccgct    4680
taccggatac ctgtccgcct ttctcccttc gggaagcgtg gcgctttctc atagctcacg    4740
ctgtaggtat ctcagttcgg tgtaggtcgt tcgctccaag ctgggctgtg tgcacgaacc    4800
ccccgttcag cccgaccgct gcgccttatc cggtaactat cgtcttgagt ccaacccggt    4860
aagacacgac ttatcgccac tggcagcagc cactggtaac aggattagca gagcgaggta    4920
tgtaggcggt gctacagagt tcttgaagtg gtggcctaac tacggctaca ctagaaggac    4980
agtatttggt atctgcgctc tgctgaagcc agttaccttc ggaaaaagag ttggtagctc    5040
ttgatccggc aaacaaacca ccgctggtag cggtggtttt tttgtttgca agcagcagat    5100
tacgcgcaga aaaaaggat ctcaagaaga tcctttgatc ttttctacgg ggtctgacgc    5160
tcagtggaac gaaaactcac gttaagggat tttggtcatg agattatcaa aaaggatctt    5220
cacctagatc cttttaaagg ccggccgcgg ccgccatcgg cattttcttt tgcgttttta    5280
tttgttaact gttaattgtc cttgttcaag gatgctgtct ttgacaacag atgttttctt    5340
gcctttgatg ttcagcagga agctcggcgc aaacgttgat tgtttgtctg cgtagaatcc    5400
tctgtttgtc atatagcttg taatcacgac attgtttcct ttcgcttgag gtacagcgaa    5460
gtgtgagtaa gtaaaggtta catcgttagg atcaagatcc attttttaaca caaggccagt    5520 tttgttcagc ggcttgtatg ggccagttaa agaattagaa acataaccaa gcatgtaaat    5580
atcgttagac gtaatgccgt caatcgtcat ttttgatccg cgggagtcag tgaacaggta    5640
ccatttgccg ttcattttaa agacgttcgc gcgttcaatt tcatctgtta ctgtgttaga    5700
tgcaatcagc ggtttcatca cttttttcag tgtgtaatca tcgtttagct caatcatacc    5760
gagagcgccg tttgctaact cagccgtgcg tttttttatcg ctttgcagaa gtttttgact    5820
ttcttgacgg aagaatgatg tgcttttgcc atagtatgct ttgttaaata aagattcttc    5880
gccttggtag ccatcttcag ttccagtgtt tgcttcaaat actaagtatt tgtggccttt    5940
atcttctacg tagtgaggat ctctcagcgt atggttgtcg cctgagctgt agttgccttc    6000
atcgatgaac tgctgtacat tttgatacgt ttttccgtca ccgtcaaaga ttgattata    6060 atcctctaca ccgttgatgt tcaaagagct gtctgatgct gatacgttaa cttgtgcagt    6120
tgtcagtgtt tgtttgccgt aatgtttacc ggagaaatca gtgtagaata aacgattt     6180 tccgtcagat gtaaatgtgg ctgaacctga ccattcttgt gtttggtctt ttaggataga    6240
atcatttgca tcgaatttgt cgctgtcttt aaagacgcgg ccagcgtttt tccagctgtc    6300
aatagaagtt tcgccgactt tttgatagaa catgtaaatc gatgtgtcat ccgcatttt    6360 aggatctccg gctaatgcaa agacgatgtg gtagccgtga tagttgcga cagtgccgtc    6420 agcgttttgt aatggccagc tgtcccaaac gtccaggcct tttgcagaag agatatttt    6480 aattgtggac gaatcaaatt cagaaacttg atattttca tttttttgct gttcagggat    6540
ttgcagcata tcatggcgtg taatatggga aatgccgtat gtttccttat atggcttttg    6600
gttcgtttct ttcgcaaacg cttgagttgc gcctcctgcc agcagtgcgg tagtaaaggt    6660
taatactgtt gcttgttttg caaactttt gatgttcatc gttcatgtct cctttttat     6720 gtactgtgtt agcggtctgc ttcttccagc cctcctgttt gaagatggca agttagttac    6780
```

```
gcacaataaa aaaagaccta aaatatgtaa ggggtgacgc caaagtatac actttgccct    6840
ttacacattt taggtcttgc ctgctttatc agtaacaaac ccgcgcgatt tacttttcga    6900
cctcattcta ttagactctc gtttggattg caactggtct attttcctct tttgtttgat    6960
agaaaatcat aaaaggattt gcagactacg ggcctaaaga actaaaaaat ctatctgttt    7020
cttttcattc tctgtatttt ttatagtttc tgttgcatgg gcataaagtt gccttttaa    7080 tcacaattca gaaaatatca taatatctca tttcactaaa taatagtgaa cggcaggtat    7140
atgtgatggg ttaaaaagga tcggcggccg ctcgatttaa atc                      7183
```